(12) United States Patent
Johnson et al.

(10) Patent No.: US 7,960,522 B2
(45) Date of Patent: Jun. 14, 2011

(54) CERTAIN AMINOALKYL GLUCOSAMINIDE PHOSPHATE COMPOUNDS AND THEIR USE

(75) Inventors: David A. Johnson, Hamilton, MT (US); David Persing, Sammamish, WA (US)

(73) Assignee: Corixa Corporation, Seattle, WA (US)

( * ) Notice: Subject to any disclaimer, the term of this patent is extended or adjusted under 35 U.S.C. 154(b) by 725 days.

(21) Appl. No.: 10/888,683

(22) Filed: Jul. 8, 2004

(65) Prior Publication Data

US 2005/0227943 A1    Oct. 13, 2005

Related U.S. Application Data

(63) Continuation-in-part of application No. 10/752,660, filed on Jan. 6, 2004, now abandoned.

(60) Provisional application No. 60/438,585, filed on Jan. 6, 2003.

(51) Int. Cl.
*C07H 17/02* (2006.01)
*A01N 43/04* (2006.01)
*A61K 31/70* (2006.01)

(52) U.S. Cl. .......................... 536/17.9; 514/25

(58) Field of Classification Search .................. None
See application file for complete search history.

(56) References Cited

U.S. PATENT DOCUMENTS

| | | | |
|---|---|---|---|
| 5,593,969 | A | 1/1997 | Kamireddy et al. |
| 6,113,918 | A | 9/2000 | Johnson et al. |
| 6,303,347 | B1 | 10/2001 | Johnson et al. |
| 6,355,257 | B1 | 3/2002 | Johnson et al. |
| 6,525,028 | B1 | 2/2003 | Johnson et al. |
| 6,699,846 | B2 | 3/2004 | Elliott et al. |
| 6,764,840 | B2 | 7/2004 | Johnson et al. |
| 6,800,613 | B2 | 10/2004 | Persing et al. |
| 6,911,434 | B2 | 6/2005 | Baldridge et al. |
| 7,030,094 | B2 | 4/2006 | Mossman et al. |
| 7,063,967 | B2 | 6/2006 | Johnson et al. |
| 7,129,269 | B2 | 10/2006 | Reed et al. |
| 2003/0092643 | A1 | 5/2003 | Johnson et al. |
| 2003/0199460 | A1 | 10/2003 | Johnson et al. |

FOREIGN PATENT DOCUMENTS

| | | |
|---|---|---|
| WO | WO 98/50399 A1 | 11/1998 |
| WO | WO 01/34617 A2 | 5/2001 |
| WO | WO 0136433 A2 * | 5/2001 |
| WO | WO 2004/005308 A2 | 1/2004 |
| WO | WO 2004/062599 A2 | 7/2004 |

OTHER PUBLICATIONS

Christ et al. Science, vol. 268, Apr. 7, 1995, pp. 80-83.*
Watanabe et al. Carbohydrate Research 333 (2001) 203-231.*
Persing, David H. et al.; "Taking toll: lipid A mimetics as adjuvants and immunomodulators"; 2002, *Trends in Microbiology*, vol. 10, No. 10, pp. S32-S37.
Stover, Axel G. et al.; "Structure-Activity Relationship of Synthetic Toll-like Receptor 4 Agonists"; 2004, *The Journal of Biological Chemistry*, vol. 279, No. 6, pp. 4440-4449.
Matsuura et al., Expression of endotoxic activities by synthetic monosaccharide Lipid A analogs with alkyl-branched acyl substituents; Infection and Immunity (1995) vol. 63 pp. 1446-1451.
Shiozaki et al., Synthesis of a 3-ether analogue of Lipid A; Carbohydrate Research 1991, vol. 222 pp. 69-82.
Mochizuki et al., Lipid A-type pyrancarboxylic acid derivatives, their synthesis and their biological activities (2000), Tetrahedron, vol. 56, pp. 7691-7703.
Lien et al., A novel synthetic acyclic Lipid A-like antagonist activates cells via the lipopolysaccharide/toll-like receptor 4 signaling pathway; J. Biol. Chem. (2001), vol. 276 pp. 1873-1880.
Watanabe et al., Synthesis of Lipid A type carboxymethyl derivatives with ether chains instead of ester chains and their LPS-antagonistic activities (2003), Carbohydrate Research vol. 338 pp. 47-54.
Johnson et al.; "Synthesis and biological evaluation of a new class of vaccine adjuvants: aminoalkyl glucosaminide 4-phosphates (AGPs)"; *Bioorg. Med. Chem. Lett.*; 9(15): 2273-2278 (1999).

* cited by examiner

*Primary Examiner* — Layla Bland
(74) *Attorney, Agent, or Firm* — Kilpatrick Townsend & Stockton LLP

(57) ABSTRACT

Compounds that are adjuvants and immunoeffectors are described and claimed. The compounds augment antibody production in immunized animals as well as stimulate cytokine production and activate macrophages. Compositions and methods for using the compounds as adjuvants and immunoeffectors are also disclosed.

11 Claims, No Drawings

CERTAIN AMINOALKYL GLUCOSAMINIDE PHOSPHATE COMPOUNDS AND THEIR USE

CROSS-REFERENCE TO RELATED APPLICATIONS

This application is a continuation-in-part of application Ser. No. 10/752,660 filed Jan. 6, 2004, which claims the priority of U.S. provisional application 60/438,585 filed Jan. 6, 2003. The contents of both of said applications are hereby incorporated herein in their entirely.

BACKGROUND OF THE INVENTION

Toll-like receptors (TLRs), have been linked to the potent innate immune response and recognize distinct structural components that are unique to pathogens; this interaction drives the immune system into an activated state, with short- and long-term consequences. There is significant interest in developing agonists and antagonists of TLRs since the pharmacological manipulation of innate immune responses may lead to more effective vaccines and novel therapeutic approaches to autoimmune, atopic, malignant and infectious diseases. The first microbial product discovered to be a Toll-like receptor agonist was LPS, a bacterial membrane component specific to gram negative bacteria, which activates Toll-like receptor 4 (TLR-4). Although LPS is a potent immunomodulatory agent, its medicinal use is limited due to its extreme toxicity, including the induction of systemic inflammatory response syndrome. The biologically active endotoxic sub-structural moiety of LPS is lipid-A, a phosphorylated, multiply fatty-acid-acylated glucosamine disaccharide that serves to anchor the entire structure in the outer membrane of Gram-negative bacteria. The toxic effects of lipid A can be ameliorated by selective chemical modification of lipid A to produce monophosphoryl lipid A compounds (MPL™ immunostimulant; Corixa Corporation; Seattle, Wash.). Methods of making and using MPL™ immunostimulant and structurally like compounds in vaccine adjuvant and other applications have been described (see, for example, U.S. Pat. Nos. 4,436,727; 4,877,611; 4,866,034 and 4,912,094; 4,987,237; Johnson et al., *J Med Chem* 42:4640-4649 (1999); Ulich and Myers, in *Vaccine Design: The Subunit and Adjuvant Approach*; Powell and Newman, Eds.; Plenum: New York, 495-524, 1995). In particular, these and other references demonstrated that MPL™ immunostimulant and related compounds had significant adjuvant activities when used in vaccine formulations with protein and carbohydrate antigens for enhancing humoral and/or cell-mediated immunity to the antigens and interact with Toll-like receptors.

Drawing from experience with MPL™ immunostimulant and other bacterial cell wall components, a family of novel synthetic compounds, the aminoalkyl glucosaminide phosphates (AGPs), were developed. AGP compounds also interact with TLR-4, as agonists and antagonists. AGPs include both acyclic and cyclic compounds (U.S. Pat. Nos. 6,113,918, and 6,303,347, WO 98/50399 published Oct. 12, 1998, WO 01/34617, published May 17, 2001, WO 01/90129, published Nov. 29, 2001, and WO 02/12258, published Feb. 14, 2002). Like MPL™ immunostimulant, these compounds have been demonstrated to retain significant adjuvant characteristics when formulated with antigens in vaccine compositions and, in addition, have similar or improved toxicity profiles when compared with MPL™ immunostimulant. AGPs also demonstrate mucosal adjuvant activity and are effective in the absence of antigen, making them attractive compounds for the prophylactic and/or therapeutic use.

Another significant advantage offered by the AGPs over MPL™ immunostimulant and the like is that the AGPs are readily producible on a commercial scale by synthetic means. Since they are produced synthetically AGPs are free of trace biological contaminants found in MPL. As such AGPs would have an advantage over MPL as vaccine adjuvants in certain settings, such as in pediatric immunization protocols where adjuvant pyrogenicity must be minimized. However, because AGPs are chemically synthesized, less then optimum compound stability may lead to the accumulation of degradation products that may result in variable biological activity and stability from lot-to-lot. From the standpoint of developing GMP processes for manufacturing of materials for human clinical trials, lot stability and lot-to-lot variability are major issues. Therefore, compounds that have increased biological activity in comparison to MPL™ immunostimulant and the like, interact with toll-like receptors and/or are optimized for large scale GPL synthesis are desirable. The present invention addresses these needs and more by providing compounds modified to enhanced biological activity, stability with increased resistance to enzymatic and chemical degradation, and/or improved safety profiles.

SUMMARY OF THE INVENTION

In one aspect, this invention comprises certain novel aminoalkyl glucosaminide phosphate compounds, as defined herein, and pharmaceutically acceptable salts thereof. The invention additionally comprises compositions containing the compounds and/or their salts, and methods of use of the compounds as adjuvants and as pharmaceutically effective compounds in their own right.

DETAILED DESCRIPTION OF THE INVENTION

The compounds of the subject invention are members of the aminoalkyl glucosaminide 4-phosphate (AGP) family. As described, below, the compounds of the invention variously possess modifications to the lengths of the six acyl chains (primary and secondary), structural modifications of the alkyl arm to include a phosphate moiety, structural modification to include a primary ether lipid at the C-3 sugar position as well as three secondary ether lipids, and/or a 6-hydroxyl blocking group.

Known chemically as ω-aminoalkyl 2-amino-2-deoxy-4-phosphono-β-D-glucopyranosides the AGPs are a class of synthetic lipid A mimetics that are structurally related to the major biologically active component of component in monophosphoryl lipid A. In AGPs the reducing sugar has been replaced with an N-[(R)-3-n-alkanoyloxytetradecanoyl]aminoalkyl aglycon unit. Like other disaccharide lipid A derivatives, the AGPs comprise six fatty acids for maximal biological activity, but unlike disaccharide derivatives, the AGPs contain a conformationally flexible β-linked aglycon unit which permits energetically favored close packing of the six fatty acyl chains. Tight packing of six fatty acids in a hexagonal array is believed to play an essential role in the bioactivity of lipid A-like molecules (Seydel et al., *Immunobiol*; 187(3-5):191-211, 1993).

The compounds of the present invention are considered to be members of the AGP family. These compounds include modifications to the lengths of the six acyl chains (primary and secondary).

In one of the broadest aspects, one feature of the invention is an AGP compound having the formula (I):

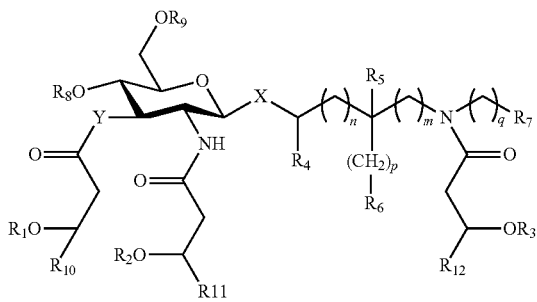

(I)

wherein X is selected from the group consisting of O and S at the axial or equatorial position; Y is selected from the group consisting of O and NH; n, m, p and q are integers from 0 to 6; $R_1$, $R_2$ and $R_3$ are the same or different and are fatty acyl residues having from 1 to about 20 carbon atoms and where one of $R_1$, $R_2$ or $R_3$ is optionally hydrogen; $R_4$ and $R_5$ are the same or different and are selected from the group consisting of H and methyl; $R_6$ and $R_7$ are the same or different and are selected from the group consisting of H, hydroxy, alkoxy, phosphono, phosphonooxy, sulfo, sulfooxy, amino, mercapto, cyano, nitro, formyl and carboxy, and esters and amides thereof; $R_8$ and $R_9$ are the same or different and are selected from the group consisting of phosphono and H, and at least one of $R_8$ and $R_9$ is phosphono; $R_{10}$, $R_{11}$ and $R_{12}$ are independently selected from straight chain unsubstituted saturated aliphatic groups having from 1 to 10 carbon atoms; or a pharmaceutically acceptable salt thereof.

In preferred embodiments of this aspect of the invention,

X and Y are preferably both oxygen atoms;

$R_1$, $R_2$ and $R_3$ are preferably normal acyl groups, which may be the same or different, and most preferably are independently selected from $C_6$-$C_{14}$ straight chain acyl groups (most preferably saturated acyl groups);

$R_{10}$, $R_{11}$ and $R_{12}$ are preferably unsubstituted saturated aliphatic (i.e., alkyl) groups having from 1 to 10, preferably from 3 to 9, more preferably from 3 to 7, carbon atoms, and most preferably are identical unsubstituted saturated aliphatic groups having from 3 to 7 carbon atoms.

Compounds 1a-c and 2a-c, and their pharmaceutically acceptable salts, are exemplary members of this type of compound (I).

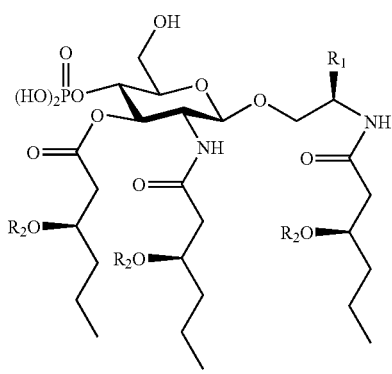

1a-c $R_1$ = $CO_2H$ or $CH_2OPO_3H_2$
$R_2$ = $C_6$, $C_{10}$, $C_{14}$ acyl

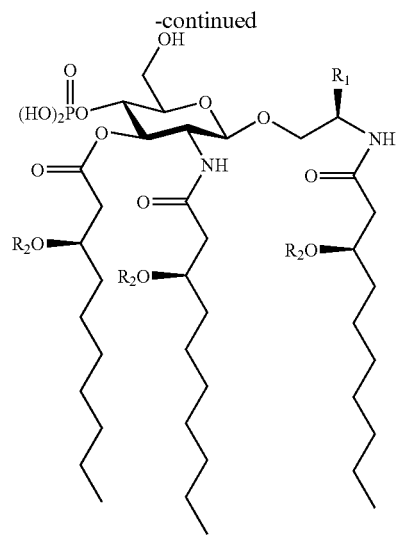

2a-c $R_1$ = $CO_2H$ or $CH_2OPO_3H_2$
$R_2$ = $C_6$, $C_{10}$, $C_{14}$ acyl

Compounds (I) of this invention thus resemble some known AGPs, except that they possess shorter primary fatty acid chains (in the previously known AGP compounds, the primary fatty acid chains have 14 carbon atoms, i.e. $R_{10}$, $R_{11}$ and $R_{12}$ are $C_{11}$ straight chain alkyl groups). Alteration in the secondary fatty acid chain length was found to impact the immune stimulating ability of AGPs and for secondary fatty acid homologs of 3-D-MPL (Johnson et al., *J Med Chem*; 42:4640-4649, 1999). Low endotoxicity of certain natural lipid A variants such as *R. sphaeroides* lipid A has been attributed in part to the presence of shorter ($C_{10}$) primary fatty acids in these molecules (Qureshi et al., *J Biol Chem*; 266 (10):6532-6538, 1991). Likewise, the low toxicity of certain *helicobacter* and pseudomonas LPS may be due to the presence of hexaacyl components containing primary fatty acids which differ in length from those found in toxic *salmonella* lipid A (Moran et al., *J Bacteriol*; 179(20):6453-6463, 1997; Kulshin et al., *Eur J Biochem*; 198(3):697-704, 1991). Although the relationship between primary acyl chain length has been investigated to a limited extent with synthetic subunit analogues of lipid A containing up to three fatty acids (Hasegawa et al., *Biosci Biotech Biochem*; 59(9):1790-1792, 1995 and Ogawa et al., *Carbohydr Res*; 220:155-164, 1991) and tetraacyl disaccharide analogues of lipid IVa, (Fukase et al., *Tetrahedron*; 54:4033-4050, 1998) to our knowledge no systematic study has ever been conducted with either the basic hexaacylated pharmacophore of lipid A or a lipid A mimetic.

Also included within the features of this invention are certain glycyl and phosphonooxyethyl (PE) compounds. These are compounds of the above formula (I) in which $R_4$, $R_5$ and $R_6$ are hydrogen, n, m and p are 0, and in which q is 1 and $R_7$ is COOH or in which q is 2 and $R_7$ is $OPO_3H_2$. These thus have the general formula (II):

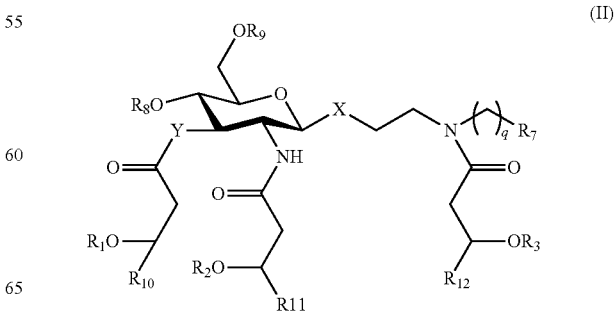

(II)

wherein X is selected from the group consisting of O and S at the axial or equatorial position; Y is selected from the group consisting of O and NH; $R_1$, $R_2$ and $R_3$ are the same or different and are fatty acyl residues having from 1 to about 20 carbon atoms and where one of $R_1$, $R_2$ or $R_3$ is optionally hydrogen; $R_4$ is selected from the group consisting of H and methyl; q is 1 and $R_7$ is COOH or q is 2 and $R_7$ is $OPO_3H_2$; $R_8$ and $R_9$ are the same or different and are selected from the group consisting of phosphono and H, and at least one of $R_8$ and $R_9$ is phosphono; and $R_{10}$, $R_{11}$ and $R_{12}$ are independently selected from straight chain unsubstituted saturated aliphatic groups having from 1 to 11 carbon atoms;

provided that if $R_7$ is COOH, then at least one of $R_{10}$, $R_{11}$ and $R_{12}$ is a straight chain unsubstituted aliphatic group having from 1 to 10 carbon atoms;

or a pharmaceutically acceptable salt thereof.

In preferred embodiments of compounds (II) of the invention,

X and Y are preferably both oxygen atoms;

$R_1$, $R_2$ and $R_3$ are preferably normal acyl groups, which may be the same or different, and preferably are independently selected from $C_6$-$C_{14}$ straight chain acyl groups, or from $C_6$-$C_{10}$ straight chain acyl groups;

if $R_7$ is COOH, then groups $R_{10}$, $R_{11}$, and $R_{12}$ are preferably unsubstituted saturated aliphatic (i.e., alkyl) groups having from 1 to 10 carbon atoms.

$R_{10}$, $R_{11}$ and $R_{12}$ of compounds (II) may be the same or different saturated aliphatic groups, but most preferably are identical unsubstituted saturated aliphatic groups.

Compounds 11a,b and 12a,b are exemplary members of this type of compound (II).

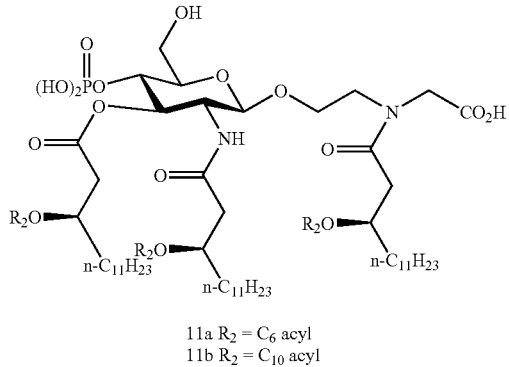

11a $R_2$ = $C_6$ acyl
11b $R_2$ = $C_{10}$ acyl

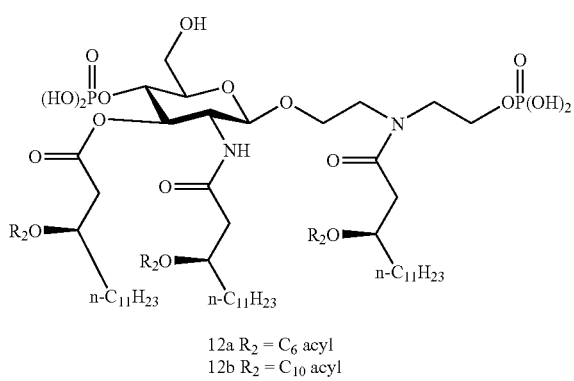

12a $R_2$ = $C_6$ acyl
12b $R_2$ = $C_{10}$ acyl

Compounds 12a, 12b contain structural modifications of the alkyl arm to include a phosphate moiety. Such compounds are considered potentially more stable than other family members. These compounds have the advantage over the seryl/serinol phosphate classes of AGPs in that they lack a stereogenic center in the aglycon unit, a feature which can complicate the synthesis and lead to hard to separate enantiomeric or diastereomeric impurities. Compounds 12a, 12b are representative of a novel class of compounds, namely those of Formula (II) in which $R_7$ is a phosphono group, and q is 2.

Another type of compound of the invention are (R)-3-alkyloxytetradecanoic acid derivatives. These have the same general formula (I) above, except that $R_1$, $R_2$ and $R_3$ are not acyl groups but are straight chain alkyl groups, making the groups $R_1O$-, $R_2O$- and $R_3O$-ether rather than carboxylic acid derivatives. In this type of compound, $R_1$, $R_2$ and $R_3$ are preferably $C_6$-$C_{11}$ alkyl groups. They may be the same or different groups, but most preferably are identical.

Such compounds have the general formula (III):

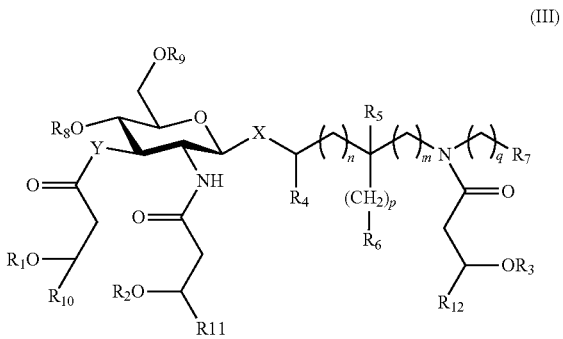

(III)

wherein X is selected from the group consisting of O and S at the axial or equatorial position; Y is selected from the group consisting of O and NH; n, m, p and q are integers from 0 to 6; $R_1$, $R_2$ and $R_3$ are the same or different and are straight chain saturated aliphatic groups (i.e., straight chain alkyl groups) having from 1 to about 20 carbon atoms and where one of $R_1$, $R_2$ or $R_3$ is optionally hydrogen; $R_4$ and $R_5$ are the same or different and are selected from the group consisting of H and methyl; $R_6$ and $R_7$ are the same or different and are selected from the group consisting of H, hydroxy, alkoxy, phosphono, phosphonooxy, sulfo, sulfooxy, amino, mercapto, cyano, nitro, formyl and carboxy, and esters and amides thereof; $R_8$ and $R_9$ are the same or different and are selected from the group consisting of phosphono and H, and at least one of $R_8$ and $R_9$ is phosphono; $R_{10}$, $R_{11}$ and $R_{12}$ are independently selected from straight chain unsubstituted saturated aliphatic groups having from 1 to 11 carbon atoms;

or a pharmaceutically acceptable salt thereof.

In preferred embodiments of compounds (III) of the invention,

X and Y are preferably both oxygen atoms; and $R_1$, $R_2$ and $R_3$, which may be the same or different, are preferably independently selected from unsubstituted $C_6$-$C_{14}$ straight chain alkyl groups, or from unsubstituted $C_6$-$C_{10}$ straight chain alkyl groups.

Compounds 18a,b are exemplary members of this group, containing three secondary ether lipids ($R_1$-$R_3$):

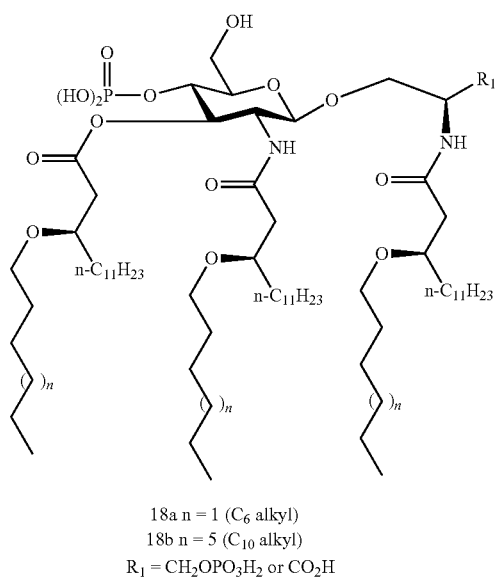

18a n = 1 (C$_6$ alkyl)
18b n = 5 (C$_{10}$ alkyl)
R$_1$ = CH$_2$OPO$_3$H$_2$ or CO$_2$H Yet another type of compound of this invention has the formula (IV):

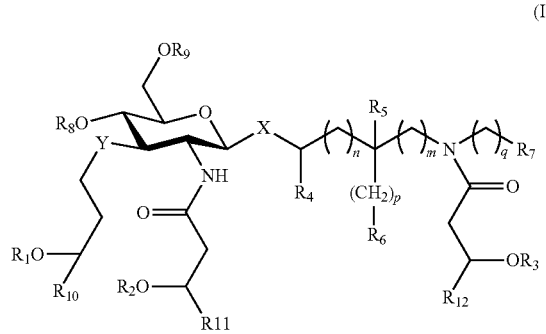

(IV)

wherein X is selected from the group consisting of O and S at the axial or equatorial position; Y is selected from the group consisting of O and NH; n, m, p and q are integers from 0 to 6; R$_1$, R$_2$ and R$_3$ are the same or different and are straight chain saturated aliphatic groups (i.e., straight chain alkyl groups) having from 1 to about 20 carbon atoms and where one of R$_1$, R$_2$ or R$_3$ is optionally hydrogen; R$_4$ and R$_5$ are the same or different and are selected from the group consisting of H and methyl; R$_6$ and R$_7$ are the same or different and are selected from the group consisting of H, hydroxy, alkoxy, phosphono, phosphonooxy, sulfo, sulfooxy, amino, mercapto, cyano, nitro, formyl and carboxy, and esters and amides thereof; R$_8$ and R$_9$ are the same or different and are selected from the group consisting of phosphono and H, and at least one of R$_8$ and R$_9$ is phosphono; R$_{10}$, R$_{11}$ and R$_{12}$ are independently selected from straight chain unsubstituted saturated aliphatic groups having from 1 to 11 carbon atoms; or a pharmaceutically acceptable salt thereof.

In preferred embodiments of compounds (IV) of the invention,

X is preferably oxygen; and

R$_1$, R$_2$ and R$_3$ may be the same or different and are most preferably independently selected from unsubstituted C$_6$-C$_{14}$ straight chain alkyl groups or from C$_6$-C$_{10}$ straight chain alkyl groups.

Compounds 20a,b are exemplary members of this class of compounds.

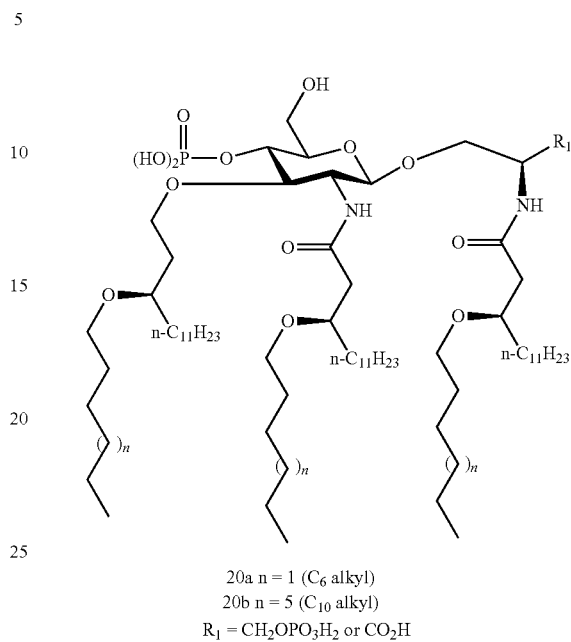

20a n = 1 (C$_6$ alkyl)
20b n = 5 (C$_{10}$ alkyl)
R$_1$ = CH$_2$OPO$_3$H$_2$ or CO$_2$H These compounds have attributes that allow resistance to unfavorable metabolism and/or aqueous hydrolysis. The selective removal of the normal fatty acids in structurally diverse lipid A molecules by human acyloxyacyl hydrolase (AOAH) to yield the antagonist lipid IVa has been postulated to have evolved as a defense mechanism to reduce lipid A toxicity (Erwin and Munford., *J Biol Chem* 265(27):16444-16449, 1990). However, the greater toxicity of naturally derived 3-D-MPL relative to that of the major hexaacyl component is likely due to the presence of less highly acylated components with structures distinct from lipid IVa (Ulrich and Myers, *Monophosphoryl lipid A as an Adjuvant. Past experiences and new directions.* In: *Vaccine Design: The Subunit and Adjuvant Approach.* Ed. Powell M. F., Newman M. J. Plenum Press, New York, 1995; p. 495-524, Johnson et al., *J Med Chem;* 42:4640-4649, 1999). The structural variability in 3-D-MPL and other lipid A preparations arises inherently from the cognate LPS as well as from ester cleavage during semi-synthetic and isolation procedures. In fact, it has been reported that facile hydrolytic cleavage of ester-linked acyl groups during the chemical synthesis of a putative *R. capsulatus* lipid A, a potent antagonist of LPS-induced TNF-α production, produces minor amounts of undesirable agonistic by-products (Christ et al., *Science;* 268:80-83, 1995). Thus, chemical and/or enzymatic instability can be the Achilles' heel of a potential lipid A-based drug containing labile ester linkages. The chemical and metabolic instability of ester-linked fatty acids present in both lipid A agonist and antagonist molecules has been overcome with hydrolytically stable analogs bearing ether linkages in place of primary and/or secondary ester-linked fatty acids (Christ et al. supra, Lien et al., *J Biol Chem;* 276(3):1873-1880, 2001).

Other compounds of the present invention have a 6-hydroxyl blocking group or a 6-substituent such as fluoro. These compounds have the formula (V):

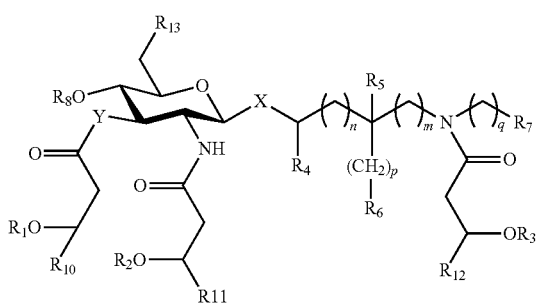

(V)

wherein X is selected from the group consisting of O and S at the axial or equatorial position; Y is selected from the group consisting of O and NH; n, m, p and q are integers from 0 to 6; $R_1$, $R_2$ and $R_3$ are the same or different and are fatty acyl residues or straight chain saturated aliphatic groups having from 1 to about 20 carbon atoms and where one of $R_1$, $R_2$ or $R_3$ is optionally hydrogen; $R_4$ and $R_5$ are the same or different and are selected from the group consisting of H and methyl; $R_6$ and $R_7$ are the same or different and are selected from the group consisting of H, hydroxy, alkoxy, phosphono, phosphonooxy, sulfo, sulfooxy, amino, mercapto, cyano, nitro, formyl and carboxy, and esters and amides thereof; $R_8$ is phosphono; $R_{13}$ is F or O-PG; PG represents a hydroxyl-protecting group as defined below, and $R_{10}$, $R_{11}$ and $R_{12}$ are independently selected from straight chain unsubstituted saturated aliphatic groups having from 1 to 11 carbon atoms;

or a pharmaceutically acceptable salt thereof.

The term "protecting group" (represented here by "PG") refers to any of a large number of groups used to replace the hydrogen of a hydroxy group, so as to block, prevent, or reduce reactivity of the group. Examples of protecting groups (and a listing of commonly used abbreviations for them) can be found in T. W. Greene and P. G. Futs, "Protective Groups in Organic Chemistry" (Wiley), Beaucage and Iyer, Tetrahedron 48:2223 (1992) and Harrison et al., Compendium of Synthetic Organic Methods, vols. 1-8 (Wiley). Representative hydroxy protecting groups include those where the hydroxy group is either acylated or alkylated, such as by the formation of ethers or esters using, for instance, methyl, acetyl, benzyl, trityl, alkyl, tetrahydropyranyl, allyl or trisubstituted silyl groups.

The choice of a protecting group for a given compound, purpose or set of conditions is within the skill of those in the art, and is done so as to protect, generally or selectively, the reactive group in question under the prevailing conditions (presence of other reactive compounds, pH, temperature, etc.). Protecting groups that may be used in this invention include methyl, phthaloyl, acetyl (Ac), benzyl (Bn), 2,2,2-trichloroethoxycarbonyl (Troc), t-butyldimethylsilyl (TBS), t-butyldiphenylsilyl (TBDPS), and 2,2,2-trichloro-1,1-dimethylethyl chloroformyl (TCBOC) groups. As is known in the art, a certain protecting group or type of group may be more suitable than others for use with a particular compound or in a given situation, and advantage is taken of these suitabilities in developing processes that involve compounds with reactive groups such as hydroxy.

In preferred embodiments of these compounds (V) of the invention,

X and Y are preferably both oxygen atoms; and $R_1$, $R_2$ and $R_3$ are preferably normal acyl or alkyl groups, and most preferably are independently selected from $C_6$-$C_{10}$ straight chain acyl groups.

Exemplary members of this group include compounds 25a,b having a methyl ether or compounds 26a,b having a fluoro group used in conjunction with seryl or serinol phosphate AGPs.

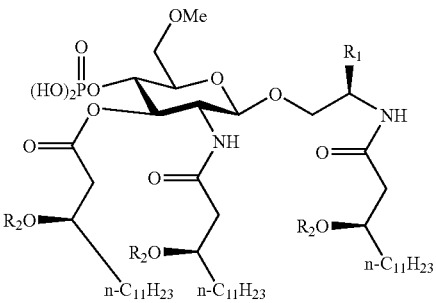

25a $R_2 = C_6$ acyl
25b $R_2 = C_{10}$ acyl $R_1 = CO_2H$ or $CH_2OPO_3H_2$

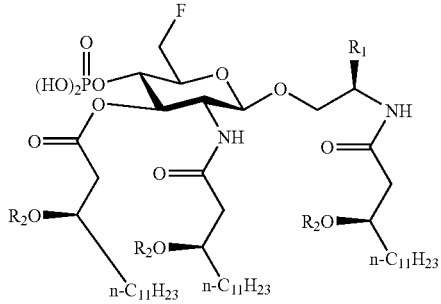

26a $R_2 = C_6$ acyl
26b $R_2 = C_{10}$ acyl

An unprotected C-6 sugar hydroxyl group can lead to minor amounts of contaminants during the synthesis of lipid A derivatives which can be difficult to remove (Christ, supra). These by-products likely arise from initial 4,6-cyclic phosphate formation and subsequent rearrangement (Imoto et al., *Tetrahedron Lett;* 29(28):2227-2230, 1988).

As discussed herein, the term "aliphatic" by itself or as part of another substituent, means, unless otherwise stated, a straight or branched chain, or cyclic hydrocarbon radical, or combination thereof, which may be fully saturated, mono- or polyunsaturated and can include di- and multivalent radicals, having the number of carbon atoms designated (i.e., $C_1$-$C_{10}$ means one to ten carbons). Examples of saturated hydrocarbon radicals include groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated aliphatic group is one having one or more double bonds or triple bonds. Examples of unsaturated aliphatic groups include vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. Typically, an aliphatic group will have from 1 to 24 carbon atoms. A "lower aliphatic" group is a shorter chain aliphatic group, generally having eight or fewer carbon atoms.

The term "acyl" refers to a group derived from an organic acid by removal of the hydroxy group. Examples of acyl groups include acetyl, propionyl, dodecanoyl, tetradecanoyl, isobutyryl, and the like. Accordingly, the term "acyl" as used herein is meant to include a group otherwise defined as —C(O)-aliphatic, where the aliphatic group is preferably a saturated aliphatic group.

The term "pharmaceutically acceptable salts" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galacturonic acids and the like (see, for example, Berge, S. M., et al, "Pharmaceutical Salts," *Journal of Pharmaceutical Science*, 66, 1-19, 1977). Certain specific compounds of the present invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers and individual isomers are all intended to be encompassed within the scope of the present invention.

The compounds of the present invention may also contain unnatural proportions of atomic isotopes at one or more of the atoms that constitute such compounds. For example, the compounds may be radiolabeled with radioactive isotopes, such as for example tritium ($^3H$), iodine-125 ($^{125}I$) or carbon-14 ($^{14}C$). All isotopic variations of the compounds of the present invention, whether radioactive or not, are intended to be encompassed within the scope of the present invention.

The compounds of the present invention can be prepared by any suitable means; see the Example section below, many of which have been described. For example, processes for preparing certain compounds useful in the present invention are described in U.S. Pat. No. 6,113,918; U.S. Pat. No. 6,303,347; and PCT/US98/09385 (WO 98/50300, Oct. 12, 1998). Still other compounds can be prepared using methods outlined in Johnson, et al., *J. Med. Chem.* 42:4640-4649 (1999), Johnson, et al., *Bioorg. Med. Chem. Lett.* 9:2273-2278 (1999), and PCT/US98/50399 (WO 98/50399, Nov. 12, 1998). In general, the synthetic methods described in the above-noted references and other synthetic methods otherwise familiar in the art are broadly applicable to the preparation of these compounds. For example, in making compounds having different acyl groups and substitutions, one of skill in the art will appreciate that the convergent methods described therein can be modified to use alternate acylating agents, or can be initiated with commercially available materials having appropriate acyl groups attached.

In compositions for eliciting or enhancing an immune response, the compounds of the subject invention are administered to a warm-blooded animal, including humans, with an antigen such as a protein or polypeptide antigen or a polynucleotide that expresses a protein or polypeptide antigen. The amount of antigen administered to elicit a desired response can be readily determined by one skilled in the art and will vary with the type of antigen administered, route of administration and immunization schedule.

Compounds of the present invention can also be administered without an exogenous antigen, to elicit immediate protection via a non-specific resistance effect, as described below; see Persing et al., WIPO Publication WO 01/90129, Nov. 29, 2001. Compounds having the ability to stimulate non-specific resistance and/or elicit an adjuvant effect can be used in rapid vaccine formulation. Administration of compounds of the present invention with antigen leads to an acquired mucosal immune response within three to four weeks. Weekly administration of such compounds, via an intranasal route for example, over a four-week period would provide rapid and durable protection by combining the protection provided by the initial innate immune response, followed by the acquired immune response to the antigen of interest.

The compounds of the present invention can be evaluated in a variety of assay formats to identify and select those having the characteristics best suited for a given application of the invention. For example, animal models can be used for identifying and evaluating cytokine release profiles into systemic circulation following administration of a compound of the present invention. In addition, various in vitro and in vivo models exist for examining changes in one or more aspects of an immune response to different antigenic components in order to identify compounds best suited for eliciting a specific immune response of interest. For example, a compound can be contacted with target cells, such as macrophages, dendritic cells or Langerhans cells in vitro, and elaborated cytokines can be measured. In addition, gene expression arrays can be used to identify specific pathways activated or inhibited by a particular compound of interest.

Cytokine induction/production can be determined using treating human blood and/or cells with compounds of the present invention and measuring induction by ELISA (R & D Systems). Such methods can also be used to determine if induction is Toll receptor-dependent. Cytotoxic T lymphocyte response following administration of the compounds of the present invention is determined by $^{51}$Cr-based cytotoxicity assay. If desired, the inventive compound's performance in this regard can be compared to other compounds known to be functional in this regard, such as lipid A, MPL, AGPs or the like. In addition, the inventive compounds may be evaluated in combination with one or more adjuvant and/or immuno-modulator agents to identify synergistic effects (see for example U.S. Pat. Nos. 6,303,347 and 6,113,918, and WO 01/90129, published Nov. 29, 2001.

Animal models such as murine influenza challenge model and murine *Listeria monocytogenes* challenge model are useful for assessing adjuvant and immunomodulator activity. Briefly, the compound is administered followed by an influenza or *L. monocytogenes* challenge. The disease index (ruffled fur, hunched posture and labored breathing), weight loss and mortality, in the case of influenza or number of colony forming units in the spleens of treated/nontreated mice, in the case of *L. monocytogenes* are monitored as an indication of protection afforded by the inventive compound administration (see for example, WO 01/90129 published Nov. 29, 2001).

As used herein, the term "polypeptide" is used in its conventional meaning, i.e., as a sequence of amino acids. The polypeptides are not limited to a specific length of the product; thus, peptides, oligopeptides, and proteins are included within the definition of polypeptide, and such terms may be used interchangeably herein unless specifically indicated otherwise. This term also does not refer to or exclude post-expression modifications of the polypeptide, for example, glycosylations, acetylations, phosphorylations and the like, as well as other modifications known in the art, both naturally occurring and non-naturally occurring. A polypeptide may be an entire protein, or a subsequence thereof. Particular polypeptides of interest in the context of this invention are amino acid subsequences comprising epitopes, i.e., antigenic determinants substantially responsible for the immunogenic properties of a polypeptide and being capable of evoking an immune response.

The polypeptides useful in the present invention are sometimes herein referred to as tumor proteins or tumor polypeptides, as an indication that their identification has been based at least in part upon their increased levels of expression in tumor samples. Thus, a "tumor polypeptide" or "tumor protein," refers generally to a polypeptide sequence of the present invention, or a polynucleotide sequence encoding such a polypeptide, that is expressed in a substantial proportion of tumor samples, for example preferably greater than about 20%, more preferably greater than about 30%, and most preferably greater than about 50% or more of tumor samples tested, at a level that is at least two fold, and preferably at least five fold, greater than the level of expression in normal tissues, as determined using a representative assay provided herein.

In certain preferred embodiments, the polypeptides of the invention are immunogenic, i.e., they react detectably within an immunoassay (such as an ELISA or T-cell stimulation assay) with antisera and/or T-cells from a patient with cancer. Screening for immunogenic activity can be performed using techniques well known to the skilled artisan. For example, such screens can be performed using methods such as those described in Harlow and Lane, *Antibodies: A Laboratory Manual*, Cold Spring Harbor Laboratory, 1988. In one illustrative example, a polypeptide may be immobilized on a solid support and contacted with patient sera to allow binding of antibodies within the sera to the immobilized polypeptide. Unbound sera may then be removed and bound antibodies detected using, for example, $^{125}$I-labeled Protein A.

As would be recognized by the skilled artisan, immunogenic portions of the polypeptides disclosed herein are also encompassed by the present invention. An "immunogenic portion," as used herein, is a fragment of an immunogenic polypeptide of the invention that itself is immunologically reactive (i.e., specifically binds) with the B-cells and/or T-cell surface antigen receptors that recognize the polypeptide. Immunogenic portions may generally be identified using well known techniques, such as those summarized in Paul, *Fundamental Immunology*, 3rd ed., 243-247 (Raven Press, 1993) and references cited therein. Such techniques include screening polypeptides for the ability to react with antigen-specific antibodies, antisera and/or T-cell lines or clones. As used herein, antisera and antibodies are "antigen-specific" if they specifically bind to an antigen (i.e., they react with the protein in an ELISA or other immunoassay, and do not react detectably with unrelated proteins). Such antisera and antibodies may be prepared as described herein, and using well-known techniques.

In one preferred embodiment, an immunogenic portion of a polypeptide of the present invention is a portion that reacts with antisera and/or T-cells at a level that is not substantially less than the reactivity of the full-length polypeptide (e.g., in an ELISA and/or T-cell reactivity assay). Preferably, the level of immunogenic activity of the immunogenic portion is at least about 50%, preferably at least about 70% and most preferably greater than about 90% of the immunogenicity for the full-length polypeptide. In some instances, preferred immunogenic portions will be identified that have a level of immunogenic activity greater than that of the corresponding full-length polypeptide, e.g., having greater than about 100% or 150% or more immunogenic activity.

In certain other embodiments, illustrative immunogenic portions may include peptides in which an N-terminal leader sequence and/or transmembrane domain have been deleted. Other illustrative immunogenic portions will contain a small N- and/or C-terminal deletion (e.g., 1-30 amino acids, preferably 5-15 amino acids), relative to the mature protein.

In another embodiment, a polypeptide composition of the invention may also comprise one or more polypeptides that are immunologically reactive with T cells and/or antibodies generated against a polypeptide of the invention, particularly a polypeptide having an amino acid sequence disclosed herein, or to an immunogenic fragment or variant thereof.

In another embodiment of the invention, polypeptides are provided that comprise one or more polypeptides that are capable of eliciting T cells and/or antibodies that are immunologically reactive with one or more polypeptides described herein, or one or more polypeptides encoded by contiguous nucleic acid sequences contained in the polynucleotides disclosed herein, or immunogenic fragments or variants thereof.

Polypeptides may comprise a signal (or leader) sequence at the N-terminal end of the protein, which co-translationally or post-translationally directs transfer of the protein. The polypeptide may also be conjugated to a linker or other sequence for ease of synthesis, purification or identification of the polypeptide (e.g., poly-His), or to enhance binding of the polypeptide to a solid support. For example, a polypeptide may be conjugated to an immunoglobulin Fc region.

Within other illustrative embodiments, a polypeptide may be a fusion polypeptide that comprises multiple polypeptides as described herein, or that comprises at least one polypeptide as described herein and an unrelated sequence, such as a known tumor protein. A fusion partner may, for example, assist in providing T helper epitopes (an immunological fusion partner), preferably T helper epitopes recognized by humans, or may assist in expressing the protein (an expression enhancer) at higher yields than the native recombinant protein. Certain preferred fusion partners are both immunological and expression enhancing fusion partners. Other fusion partners may be selected so as to increase the solubility of the polypeptide or to enable the polypeptide to be targeted to desired intracellular compartments. Still further fusion partners include affinity tags, which facilitate purification of the polypeptide.

Fusion polypeptides may generally be prepared using standard techniques, including chemical conjugation. Preferably, a fusion polypeptide is expressed as a recombinant polypeptide, allowing the production of increased levels, relative to a non-fused polypeptide, in an expression system. Briefly, DNA sequences encoding the polypeptide components may be assembled separately, and ligated into an appropriate expression vector. The 3' end of the DNA sequence encoding one polypeptide component is ligated, with or without a peptide linker, to the 5' end of a DNA sequence encoding the second polypeptide component so that the reading frames of the sequences are in phase. This permits translation into a single fusion polypeptide that retains the biological activity of both component polypeptides.

A peptide linker sequence may be employed to separate the first and second polypeptide components by a distance sufficient to ensure that each polypeptide folds into its secondary and tertiary structures. Such a peptide linker sequence is incorporated into the fusion polypeptide using standard techniques well known in the art. Suitable peptide linker sequences may be chosen based on the following factors: (1) their ability to adopt a flexible extended conformation; (2) their inability to adopt a secondary structure that could interact with functional epitopes on the first and second polypeptides; and (3) the lack of hydrophobic or charged residues that might react with the polypeptide functional epitopes. Preferred peptide linker sequences contain Gly, Asn and Ser residues. Other near neutral amino acids, such as Thr and Ala may also be used in the linker sequence. Amino acid sequences which may be usefully employed as linkers include those disclosed in Maratea et al., *Gene* 40:39-46, 1985; Murphy et al., *Proc. Natl. Acad. Sci. USA* 83:8258-8262, 1986; U.S. Pat. No. 4,935,233 and U.S. Pat. No. 4,751,180. The linker sequence may generally be from 1 to about 50 amino acids in length. Linker sequences are not required when the first and second polypeptides have non-essential N-terminal amino acid regions that can be used to separate the functional domains and prevent steric interference.

The ligated DNA sequences are operably linked to suitable transcriptional or translational regulatory elements. The regulatory elements responsible for expression of DNA are located only 5' to the DNA sequence encoding the first polypeptides. Similarly, stop codons required to end translation and transcription termination signals are only present 3' to the DNA sequence encoding the second polypeptide.

The fusion polypeptide can comprise a polypeptide as described herein together with an unrelated immunogenic protein, such as an immunogenic protein capable of eliciting a recall response. Examples of such proteins include tetanus, tuberculosis and hepatitis proteins (see, for example, Stoute et al. *New Engl. J. Med.*, 336:86-91, 1997).

In one preferred embodiment, the immunological fusion partner is derived from a *Mycobacterium* sp., such as a *Mycobacterium tuberculosis*-derived Ra12 fragment. Ra12 compositions and methods for their use in enhancing the expression and/or immunogenicity of heterologous polynucleotide/polypeptide sequences is described in U.S. Patent Application 60/158,585. Briefly, Ra12 refers to a polynucleotide region that is a subsequence of a *Mycobacterium tuberculosis* MTB32A nucleic acid. MTB32A is a serine protease of 32 KD molecular weight encoded by a gene in virulent and avirulent strains of *M. tuberculosis*. The nucleotide sequence and amino acid sequence of MTB32A have been described (for example, U.S. Patent Application 60/158,585; see also, Skeiky et al., *Infection and Immun.* (1999) 67:3998-4007). C-terminal fragments of the MTB32A coding sequence express at high levels and remain as a soluble polypeptides throughout the purification process. Moreover, Ra12 may enhance the immunogenicity of heterologous immunogenic polypeptides with which it is fused. One preferred Ra12 fusion polypeptide comprises a 14 KD C-terminal fragment corresponding to amino acid residues 192 to 323 of MTB32A. Other preferred Ra12 polynucleotides generally comprise at least about 15 consecutive nucleotides, at least about 30 nucleotides, at least about 60 nucleotides, at least about 100 nucleotides, at least about 200 nucleotides, or at least about 300 nucleotides that encode a portion of a Ra12 polypeptide. Ra12 polynucleotides may comprise a native sequence (i.e., an endogenous sequence that encodes a Ra12 polypeptide or a portion thereof) or may comprise a variant of such a sequence. Ra12 polynucleotide variants may contain one or more substitutions, additions, deletions and/or insertions such that the biological activity of the encoded fusion polypeptide is not substantially diminished, relative to a fusion polypeptide comprising a native Ra12 polypeptide. Variants preferably exhibit at least about 70% identity, more preferably at least about 80% identity and most preferably at least about 90% identity to a polynucleotide sequence that encodes a native Ra12 polypeptide or a portion thereof.

Within other preferred embodiments, an immunological fusion partner is derived from protein D, a surface protein of the gram-negative bacterium *Haemophilus influenza* B (WO 91/18926). Preferably, a protein D derivative comprises approximately the first third of the protein (e.g., the first N-terminal 100-110 amino acids), and a protein D derivative may be lipidated. Within certain preferred embodiments, the first 109 residues of a Lipoprotein D fusion partner is included on the N-terminus to provide the polypeptide with additional exogenous T-cell epitopes and to increase the expression level in *E. coli* (thus functioning as an expression enhancer). The lipid tail ensures optimal presentation of the antigen to antigen presenting cells. Other fusion partners include the non-structural protein from influenzae virus, NS1 (hemaglutinin). Typically, the N-terminal 81 amino acids are used, although different fragments that include T-helper epitopes may be used.

In another embodiment, the immunological fusion partner is the protein known as LYTA, or a portion thereof (preferably a C-terminal portion). LYTA is derived from *Streptococcus pneumoniae*, which synthesizes an N-acetyl-L-alanine amidase known as amidase LYTA (encoded by the LytA gene; Gene 43:265-292, 1986). LYTA is an autolysin that specifically degrades certain bonds in the peptidoglycan backbone. The C-terminal domain of the LYTA protein is responsible for the affinity to the choline or to some choline analogues such as DEAE. This property has been exploited for the development of *E. coli* C-LYTA expressing plasmids useful for expression of fusion proteins. Purification of hybrid proteins containing the C-LYTA fragment at the amino terminus has been described (see *Biotechnology* 10:795-798, 1992). Within a preferred embodiment, a repeat portion of LYTA may be incorporated into a fusion polypeptide. A repeat portion is found in the C-terminal region starting at residue 178. A particularly preferred repeat portion incorporates residues 188-305.

Yet another illustrative embodiment involves fusion polypeptides, and the polynucleotides encoding them, wherein the fusion partner comprises a targeting signal capable of directing a polypeptide to the endosomal/lysosomal compartment, as described in U.S. Pat. No. 5,633,234. An immunogenic polypeptide of the invention, when fused with this targeting signal, will associate more efficiently with MHC class II molecules and thereby provide enhanced in vivo stimulation of $CD4^+$ T-cells specific for the polypeptide.

Polypeptides of the invention are prepared using any of a variety of well known synthetic and/or recombinant techniques. Polypeptides, portions and other variants generally less than about 150 amino acids can be generated by synthetic means, using techniques well known to those of ordinary skill in the art. In one illustrative example, such polypeptides are synthesized using any of the commercially available solid-phase techniques, such as the Merrifield solid-phase synthesis method, where amino acids are sequentially added to a growing amino acid chain. See Merrifield, *J. Am. Chem. Soc.* 85:2149-2146, 1963. Equipment for automated synthesis of polypeptides is commercially available from suppliers such as Perkin Elmer/Applied BioSystems Division (Foster City, Calif.), and may be operated according to the manufacturer's instructions.

In general, polypeptide compositions (including fusion polypeptides) of the invention are isolated. An "isolated" polypeptide is one that is removed from its original environment. For example, a naturally-occurring protein or polypeptide is isolated if it is separated from some or all of the coexisting materials in the natural system. Preferably, such polypeptides are also purified, e.g., are at least about 90% pure, more preferably at least about 95% pure and most preferably at least about 99% pure.

The present invention, in other aspects, provides compounds comprising one or more polynucleotide that encodes a polypeptide antigen as set forth herein above. The terms "DNA" and "polynucleotide" are used essentially interchangeably herein to refer to a DNA molecule that has been isolated free of total genomic DNA of a particular species. "Isolated," as used herein, means that a polynucleotide is substantially away from other coding sequences, and that the DNA molecule does not contain large portions of unrelated coding DNA, such as large chromosomal fragments or other functional genes or polypeptide coding regions. Of course, this refers to the DNA molecule as originally isolated, and does not exclude genes or coding regions later added to the segment by the hand of man.

Polynucleotides may comprise a native sequence (i.e., an endogenous sequence that encodes a polypeptide/protein of the invention or a portion thereof) or may comprise a sequence that encodes a variant or derivative, preferably and immunogenic variant or derivative, of such a sequence. Typically, polynucleotide variants will contain one or more substitutions, additions, deletions and/or insertions, preferably such that the immunogenicity of the polypeptide encoded by the variant polynucleotide is not substantially diminished relative to a polypeptide encoded by a polynucleotide sequence specifically set forth herein). The term "variants" should also be understood to encompass homologous genes of xenogenic origin.

In certain preferred embodiments, the polynucleotides described above, e.g., polynucleotide variants, fragments and hybridizing sequences, encode polypeptides that are immunologically cross-reactive with an antigenic or immunogenic polypeptide as set forth herein above. In other preferred embodiments, such polynucleotides encode polypeptides that have a level of immunogenic activity of at least about 50%, preferably at least about 70%, and more preferably at least about 90% of that for a polypeptide sequence specifically set forth herein.

The polynucleotides of the present invention, or fragments thereof, regardless of the length of the coding sequence itself, may be combined with other DNA sequences, such as promoters, polyadenylation signals, additional restriction enzyme sites, multiple cloning sites, other coding segments, and the like, such that their overall length may vary considerably. It is therefore contemplated that a nucleic acid fragment of almost any length may be employed, with the total length preferably being limited by the ease of preparation and use in the intended recombinant DNA protocol. For example, illustrative polynucleotide segments with total lengths of about 10,000, about 5000, about 3000, about 2,000, about 1,000, about 500, about 200, about 100, about 50 base pairs in length, and the like, (including all intermediate lengths) are contemplated to be useful in many implementations of this invention.

Polynucleotides compositions of the present invention may be identified, prepared and/or manipulated using any of a variety of well established techniques (see generally, Sambrook et al., *Molecular Cloning: A Laboratory Manual*, Cold Spring Harbor Laboratories, Cold Spring Harbor, N.Y., 1989, and other like references). For example, a polynucleotide may be identified, as described in more detail below, by screening a microarray of cDNAs for tumor-associated expression (i.e., expression that is at least two fold greater in a tumor than in normal tissue, as determined using a representative assay provided herein). Such screens may be performed, for example, using the microarray technology of Affymetrix, Inc. (Santa Clara, Calif.) according to the manufacturer's instructions (and essentially as described by Schena et al., *Proc. Natl. Acad. Sci. USA* 94:10614-10619, 1996 and Heller et al., *Proc. Natl. Acad. Sci. USA* 94:2150-2155, 1997). Alternatively, polynucleotides may be amplified from cDNA prepared from cells expressing the proteins described herein, such as tumor cells.

Many template dependent processes are available to amplify a target sequence of interest present in a sample. One of the best known amplification methods is the polymerase chain reaction (PCR™) which is described in detail in U.S. Pat. Nos. 4,683,195, 4,683,202 and 4,800,159. Briefly, in PCR™, two primer sequences are prepared which are complementary to regions on opposite complementary strands of the target sequence. An excess of deoxynucleoside triphosphates is added to a reaction mixture along with a DNA polymerase (e.g., Taq polymerase). If the target sequence is present in a sample, the primers will bind to the target and the polymerase will cause the primers to be extended along the target sequence by adding on nucleotides. By raising and lowering the temperature of the reaction mixture, the extended primers will dissociate from the target to form reaction products, excess primers will bind to the target and to the reaction product and the process is repeated. Preferably reverse transcription and PCR™ amplification procedure may be performed in order to quantify the amount of mRNA amplified. Polymerase chain reaction methodologies are well known in the art.

Any of a number of other template dependent processes, many of which are variations of the PCR™ amplification technique, are readily known and available in the art. Illustratively, some such methods include the ligase chain reaction (referred to as LCR), described, for example, in Eur. Pat. Appl. Publ. No. 320,308 and U.S. Pat. No. 4,883,750; Qbeta Replicase, described in PCT Intl. Pat. Appl. Publ. No. PCT/US87/00880; Strand Displacement Amplification (SDA) and Repair Chain Reaction (RCR). Still other amplification methods are described in Great Britain Pat. Appl. No. 2 202 328, and in PCT Intl. Pat. Appl. Publ. No. PCT/US89/01025. Other nucleic acid amplification procedures include transcription-based amplification systems (TAS) (PCT Intl. Pat. Appl. Publ. No. WO 88/10315), including nucleic acid sequence based amplification (NASBA) and 3SR. Eur. Pat. Appl. Publ. No. 329,822 describes a nucleic acid amplification process involving cyclically synthesizing single-stranded RNA ("ssRNA"), ssDNA, and double-stranded DNA (dsDNA). PCT Intl. Pat. Appl. Publ. No. WO 89/06700 describes a nucleic acid sequence amplification scheme based on the hybridization of a promoter/primer sequence to a target single-stranded DNA ("ssDNA") followed by transcription of many RNA copies of the sequence. Other amplification methods such as "RACE" (Frohman, 1990), and "one-sided PCR" (Ohara, 1989) are also well known to those of skill in the art.

An amplified portion of a polynucleotide of the present invention may be used to isolate a full length gene from a suitable library (e.g., a tumor cDNA library) using well known techniques. Within such techniques, a library (cDNA or genomic) is screened using one or more polynucleotide probes or primers suitable for amplification. Preferably, a library is size-selected to include larger molecules. Random primed libraries may also be preferred for identifying 5' and upstream regions of genes. Genomic libraries are preferred for obtaining introns and extending 5' sequences.

For hybridization techniques, a partial sequence may be labeled (e.g., by nick-translation or end-labeling with $^{32}P$) using well known techniques. A bacterial or bacteriophage library is then generally screened by hybridizing filters containing denatured bacterial colonies (or lawns containing phage plaques) with the labeled probe (see Sambrook et al., *Molecular Cloning: A Laboratory Manual*, Cold Spring Harbor Laboratories, Cold Spring Harbor, N.Y., 1989). Hybridizing colonies or plaques are selected and expanded, and the DNA is isolated for further analysis. cDNA clones may be analyzed to determine the amount of additional sequence by, for example, PCR using a primer from the partial sequence and a primer from the vector. Restriction maps and partial sequences may be generated to identify one or more overlapping clones. The complete sequence may then be determined using standard techniques, which may involve generating a series of deletion clones. The resulting overlapping sequences can then assembled into a single contiguous sequence. A full-length cDNA molecule can be generated by ligating suitable fragments, using well known techniques.

Alternatively, amplification techniques, such as those described above, can be useful for obtaining a full length coding sequence from a partial cDNA sequence. One such amplification technique is inverse PCR (see Triglia et al., *Nuc. Acids Res.* 16:8186, 1988), which uses restriction enzymes to generate a fragment in the known region of the gene. The fragment is then circularized by intramolecular ligation and used as a template for PCR with divergent primers derived from the known region. Within an alternative approach, sequences adjacent to a partial sequence may be retrieved by amplification with a primer to a linker sequence and a primer specific to a known region. The amplified sequences are typically subjected to a second round of amplification with the same linker primer and a second primer specific to the known region. A variation on this procedure, which employs two primers that initiate extension in opposite directions from the known sequence, is described in WO 96/38591. Another such technique is known as "rapid amplification of cDNA ends" or RACE. This technique involves the use of an internal primer and an external primer, which hybridizes to a polyA region or vector sequence, to identify sequences that are 5' and 3' of a known sequence. Additional techniques include capture PCR (Lagerstrom et al., *PCR Methods Applic.* 1:111-19, 1991) and walking PCR (Parker et al., *Nucl. Acids. Res.* 19:3055-60, 1991). Other methods employing amplification may also be employed to obtain a full-length cDNA sequence.

In certain instances, it is possible to obtain a fill length cDNA sequence by analysis of sequences provided in an expressed sequence tag (EST) database, such as that available from GenBank. Searches for overlapping ESTs may generally be performed using well-known programs (e.g., NCBI BLAST searches), and such ESTs may be used to generate a contiguous full length sequence. Full-length DNA sequences may also be obtained by analysis of genomic fragments.

In other embodiments of the invention, polynucleotide sequences or fragments thereof which encode polypeptides set forth herein above, or fusion proteins or functional equivalents thereof, may be used in recombinant DNA molecules to direct expression of a polypeptide in appropriate host cells. Due to the inherent degeneracy of the genetic code, other DNA sequences that encode substantially the same or a functionally equivalent amino acid sequence may be produced and these sequences may be used to clone and express a given polypeptide.

Sequences encoding a desired polypeptide may be synthesized, in whole or in part, using chemical methods well known in the art (see Caruthers, M. H. et al. (1980) *Nucl. Acids Res. Symp. Ser.* 215-223, Horn, T. et al. (1980) *Nucl. Acids. Symp. Ser.* 225-232).

In order to express a desired polypeptide, the nucleotide sequences encoding the polypeptide, or functional equivalents, may be inserted into appropriate expression vector, i.e., a vector that contains the necessary elements for the transcription and translation of the inserted coding sequence. Methods well known to those skilled in the art may be used to construct expression vectors containing sequences encoding a polypeptide of interest and appropriate transcriptional and translational control elements. These methods include in vitro recombinant DNA techniques, synthetic techniques, and in vivo genetic recombination. Such techniques are described, for example, in Sambrook, J. et al. (1989) Molecular Cloning, A Laboratory Manual, Cold Spring Harbor Press, Plainview, N.Y., and Ausubel, F. M. et al. (1989) Current Protocols in Molecular Biology, John Wiley & Sons, New York. N.Y.

The "control elements" or "regulatory sequences" present in an expression vector are those non-translated regions of the vector—enhancers, promoters, 5' and 3' untranslated regions—which interact with host cellular proteins to carry out transcription and translation. Such elements may vary in their strength and specificity. Depending on the vector system and host utilized, any number of suitable transcription and translation elements, including constitutive and inducible promoters, may be used.

In mammalian cells, a number of viral-based expression systems are generally available. For example, in cases where an adenovirus is used as an expression vector, sequences encoding a polypeptide of interest may be ligated into an adenovirus transcription/translation complex consisting of the late promoter and tripartite leader sequence. Insertion in a non-essential E1 or E3 region of the viral genome may be used to obtain a viable virus that is capable of expressing the polypeptide in infected host cells (Logan, J. and Shenk, T. (1984) *Proc. Natl. Acad. Sci.* 81:3655-3659). In addition, transcription enhancers, such as the Rous sarcoma virus (RSV) enhancer, may be used to increase expression in mammalian host cells.

Specific initiation signals may also be used to achieve more efficient translation of sequences encoding a polypeptide of interest. Such signals include the ATG initiation codon and adjacent sequences. In cases where sequences encoding the polypeptide, its initiation codon, and upstream sequences are inserted into the appropriate expression vector, no additional transcriptional or translational control signals may be needed. However, in cases where only coding sequence, or a portion thereof, is inserted, exogenous translational control signals including the ATG initiation codon should be provided. Furthermore, the initiation codon should be in the correct reading frame to ensure translation of the entire insert. Exogenous translational elements and initiation codons may be of various origins, both natural and synthetic. The efficiency of expression may be enhanced by the inclusion of enhancers which are appropriate for the particular cell system which is used, such as those described in the literature (Scharf, D. et al. (1994) *Results Probl. Cell Differ.* 20:125-162).

A variety of protocols for detecting and measuring the expression of polynucleotide-encoded products, using either polyclonal or monoclonal antibodies specific for the product are known in the art. Examples include enzyme-linked immunosorbent assay (ELISA), radioimmunoassay (RIA), and fluorescence activated cell sorting (FACS). A two-site, monoclonal-based immunoassay utilizing monoclonal antibodies reactive to two non-interfering epitopes on a given polypeptide may be preferred for some applications, but a competitive binding assay may also be employed. These and other assays are described, among other places, in Hampton, R. et al. (1990; Serological Methods, a Laboratory Manual, APS Press, St Paul. Minn.) and Maddox, D. E. et al. (1983; *J. Exp. Med.* 158:1211-1216).

Pharmaceutical Compositions and Methods

It will be understood that, if desired, the compounds disclosed herein may be administered in combination with other therapeutic modalities, such as antimicrobial, antiviral and antifungal compounds or therapies, various DNA-based therapeutics, RNA-based therapeutics, polypeptide-based therapeutics and/or with other immunoeffectors. In fact, essentially any other component may also be included, given that the additional component(s) do not cause a significant adverse effect upon contact with the target cells or host tissues. The compositions may thus be delivered along with various other agents as required or desired for the specific embodiment(s) of the invention being implemented. Illustratively, the pharmaceutical compositions of the invention can include, or be used in conjunction with, DNA encoding one o'r more therapeutic proteins, antisense RNAs, ribozymes or the like.

In one aspect, compounds of the invention and compositions comprising them may be administered together with an antigen, to provide an adjuvant or enhancing effect of the antigen, i.e. to enhance the immune response of the patient or subject. In another aspect, compounds and compositions of the invention are administered in the absence of exogenous antigen, for the therapeutic effect of the compound itself.

In another aspect, wherein the compound or composition is administered without exogenous antigen, the present invention provides methods for treating, ameliorating and/or substantially preventing infectious diseases in eukaryotic subjects, particularly in animals, preferably in humans. Given the importance of TLR-mediated signalling in the innate immune response to microbial challenge, the ability to stimulate such pathways selectively and with minimal toxicity represents a powerful approach for prophylactic and/or therapeutic treatment modalities against a wide range of infectious agents.

The methods described herein are applicable against essentially any type of infectious agent, including bacteria, viruses, parasites, and fungi. Illustratively, the invention is useful for the prophylactic and/or therapeutic treatment of bacterial infections by species from *Pseudomonas, Escherichia, Klebsiella, Enterobacter, Proteus, Serratia, Candida*, Staphylococci, Streptococci, *Chlamydia, Mycoplasma* and numerous others. Illustrative viral conditions that may be treated in accordance with the invention include those caused, for example, by Influenza viruses, Adenoviruses, parainfluenza viruses, Rhinoviruses, respiratory syncytial viruses (RSVs), Herpes viruses, Cytomegaloviruses, Hepatitis viruses, e.g., Hepatitis B and C viruses, and others. Illustrative fungi include, for example, *Aspergillis, Candida albicans, Cryptococcus neoformans, Coccidioides immitus*, and others.

In one illustrative embodiment, the invention provides methods for the treatment of subjects, particularly immunocompromised subjects that have developed or are at risk for developing infections, such as nosocomial bacterial and viral infections. About 2 million of the 40 million individuals hospitalized every year develop nosocomial infection during their stay and about 1% of these, or about 400,000 patients, develop nosocomial pneumonia, more than 7000 of which die. This makes nosocomial pneumonia the leading cause of death in hospital-acquired infections. Thus, this embodiment fills a significant need for effective prophylactic approaches in the treatment of nosocomial infections.

In a related embodiment, the present invention provides prophylactic treatments for immunocompromised patients, such as HIV-positive patients, who have developed or are at risk for developing pneumonia from either an opportunistic infection or from the reactivation of a suppressed or latent infection. In 1992, about 20,000 cases of *Pneumocystis carinii* infections in AIDS patients were reported in the U.S. alone. Additionally, 60-70% of all AIDS patients get *P. carinii* at some time during their illness. Thus, the present invention in this embodiment provides effective prophylactic methods for this at-risk population.

In another related embodiment, the methods of the present invention are used for treating other patient populations that may be immunocompromised and/or at risk for developing infectious diseases, including, for example, patients with cystic fibrosis, chronic obstructive pulmonary disease and other immunocompromised and/or institutionalized patients.

In another aspect of the invention, compounds and compositions of the invention are employed (without exogenous antigen) in methods for treating, ameliorating or substantially preventing allergic disorders and conditions, such as sinusitis, chronic rhinosinusitis, asthma, atopic dermatitis and psoriasis. This approach is based at least in part on the ability of the compounds to activate the production of cytokines from target cells that can compete with stereotypic allergic-type cytokine responses characterized by IL-4 production or hyperresponsiveness to IL-4 activity. Administration of certain of the mono- and disaccharide compounds disclosed herein results in IFN-gamma and IL-12 expression from antigen processing and presenting cells, as well as other cells, resulting in down regulation of cytokines associated with allergic responses such as IL-4, 5, 6, 10 and 13.

In still another aspect of the invention, compounds and compositions of the invention are employed (without exogenous antigen) in methods for treating autoimmune diseases and conditions. The compounds for use in this embodiment will typically be selected from those capable of antagonizing, inhibiting or otherwise negatively modulating one or more Toll-like receptors, particularly Tlr2 and/or Tlr4, such that an autoimmune response associated with a given condition is ameliorated or substantially prevented. Illustratively, the methods provided by this embodiment can be used in the treatment of conditions such as inflammatory bowel disease, rheumatoid arthritis, chronic arthritis, multiple sclerosis and psoriasis.

The compounds of the subject invention also may be used as adjuvants and immunoeffectors which enhance the generation of antibody in immunized animals, stimulate the production of cytokines and stimulate a cell-mediated immune response including a cytotoxic T-lymphocyte response.

In methods according to the invention, for example, for effecting the immune response of an individual, the compounds and compositions of the subject invention can be formulated with a pharmaceutically acceptable carrier for injection or ingestion. As used herein, "pharmaceutically acceptable carrier" means a medium that does not interfere with the immunomodulatory activity of the active ingredient and is not toxic to the patient to whom it is administered. Pharmaceutically acceptable carriers include oil-in-water or water-in-oil emulsions, aqueous compositions, liposomes, microbeads and microsomes. For example, the carrier may be a microsphere or microparticle having a compound of this invention within the matrix of the sphere or particle or adsorbed on the surface of the sphere or particle. The carrier may also be an aqueous solution or micellar dispersion containing triethylamine, triethanolamine or other agent that renders the formulation alkaline in nature, or a suspension containing aluminum hydroxide, calcium hydroxide, calcium phosphate or tyrosine adsorbate. Carriers may also include all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated.

Formulations of the compounds of the subject invention that can be administered parenterally, i.e. intraperitoneally, subcutaneously or intramuscularly include the following preferred carriers. Examples of preferred carriers for subcutaneous use include a phosphate buffered saline (PBS) solution and 0.01-0.1% triethanolamine in USP Water for Injection. Suitable carriers for intramuscular injection include 10% USP ethanol, 40% propylene glycol and the balance an acceptable isotonic solution such as 5% dextrose.

Examples of preferred carriers for intravenous use include 10% USP ethanol, 40% USP propylene glycol and the balance USP Water for Injection. Another acceptable carrier includes 10% USP ethanol and USP Water for Injection; yet another acceptable carrier is 0.01-0.1% triethanolamine in USP Water for Injection. Pharmaceutically acceptable parenteral solvents are such as to provide a solution or dispersion may be filtered through a 5 micron filter without removing the active ingredient.

A preferred method of administration of the compositions of this invention is mucosal administration, particularly intranasal administration or administration by inhalation (pulmonary administration). Pulmonary drug delivery can be achieved by several different approaches, including liquid nebulizers, aerosol-based metered dose inhalers (MDIs), and dry powder dispersion devices. Compositions for use in administrations of this type are typically dry powders or aerosols. For administration of aerosols, which is the preferred method of administration of this invention, the compositions are delivered by inhalers, some types of which are described below.

Dry powders contain, in addition to the active ingredient, a carrier, an absorption enhancer, and optionally other ingredients. The carrier is, for example, a mono-, di- or polysaccharide, a sugar alcohol or another polyol. Suitable carriers include lactose, glucose, raffinose, melezitose, lactitol, maltitol, trehalose, sucrose, mannitol; and starch. Lactose is particularly preferred, especially in the form of its monohydrate. Also included are absorption enhancers such as polypeptides, surfactants, alkyl glycosides, amine salts of fatty acids or phospholipids. The ingredients of the formulation typically must be in a finely divided form, i.e. their volume median diameter should generally be from about 30 to about 200 microns, as measured by a laser diffraction instrument or a coulter counter. The desired particle size may be produced using methods known in the art, e.g. milling, micronization or direct precipitation.

The intranasal route of administration provides numerous advantages over many other forms of administration for the compounds of this invention. For instance, one advantage of intranasal administration is convenience. An injectable system requires sterilization of the hypodermic syringe and in the institutional setting, leads to concerns among medical personnel about the risk of contracting disease by being accidentally stuck by a contaminated needle. Strict requirements for the safe disposal of the used needle and syringe must also be imposed in the institutional setting. In contrast, intranasal administration requires little time on the part of the patient and the attending medical personnel, and is far less burdensome on the institution than injectables.

A second important advantage of intranasal administration is patient acceptance of the drug delivery system. Intranasal administration is perceived as non-invasive, is not accompanied by pain, has no significant after-effects and produces the gratification of prompt relief in the patient exhibiting the symptom. This is of particular advantage when the patient is a child. Another important consideration is that the patient may be able to self-administer the prescribed dosage(s) of nasal spray.

For intranasal administration the compositions of this invention may be formulated as liquids or as solids. Such compositions may contain one or more adjuvants, agents for enhancing absorption of the active ingredients by permeation across the nasal membrane, and (for liquid compositions) an aqueous diluent, for instance water. Alternatively, the diluent may comprise an aqueous buffer such as phosphate buffer. The composition may further optionally include one or more polyhydric alcohols and one or more preservative agents such as, for example, gentamicin, bacitracin (0.005%), or cresol. The compositions may be administered to the nasal cavity in the form of a spray by using an atomizer, nebulizer, sprayer, dropper or other device which insures contact of the solution with the nasal mucous membrane. The device may be a simple one such as a simple nasal sprayer that may be used by the patient, or may be a more elaborate instrument for more accurate dispensing of the compositions, that may be used in a physician's office or a medical facility.

Nasal powder compositions can be made by mixing the active agent and the excipient, both possessing the desired particle size. Firstly, a solution of the active agent and the cyclodextrin excipients made, followed by precipitation, filtration and pulverization. It is also possible to remove the solvent by freeze drying, followed by pulverization of the powder in the desired particle size by using conventional techniques, known from the pharmaceutical literature. The final step is size classification for instance by sieving, to get particles that are preferably between 30 and 200 microns in diameter. Powders can be administered using a nasal insufflator, or they may be placed in a capsule set in an inhalation or insufflation device. A needle is penetrated through the capsule to make pores at the top and the bottom of the capsule and air is sent to blow out the powder particles. Powder formulation can also be administered in a jet-spray of an inert gas or suspended in liquid organic fluids.

In a specific embodiment, the pharmaceutical composition can be delivered in a controlled or sustained release system. In one embodiment, a pump may be used to achieve a controlled or sustained release (see Langer, Science, 249:1527-1533 (1990); Sefton, 1987, CRC Crit. Ref. Biomed. Eng. 14:10; Buschwald et al., 1980, Surgery 88:507; Saudek et al., 1989 N. Engl. J. Med. 321:574). In another embodiment, polymeric materials can be used to achieve controlled or sustained release of the κ-Opioid receptor agonist and/or opioid antagonist (see e.g., Medical Applications of Controlled Release, Langer and Wise (eds.), CRC Pres., Boca Raton, Fla. 1974); Controlled Drug Bioavailability, Drug Product Design and Performance, Smolen and Ball (eds.), Wiley, New York (1984); Ranger and Peppas, 1983, J. Macromol. Sci. Rev. Macrol. Chem. 23:61; see also Levy et al., 1985 Science 228:190; During et al., 1989, Ann. Neurol. 25:351; Howard et al., 1989, J. Neurosurg. 71:105; U.S. Pat. No. 5,679,377; U.S. Pat. No. 5,916,597, U.S. Pat. No. 5,912,015; U.S. Pat. No. 5,989,463; U.S. Pat. No. 5,128,326; PCT Publication No. WO 99/12154; and PCT Publication No. WO 99/20253). Examples of polymers used in sustained release formulations include, but are not limited to, poly(2-hydroxy ethyl methacrylate), poly(methyl methacrylate), poly(acrylic acid), poly (ethylene-co-vinyl acetate), poly(methacrylic acid), polyglycolides (PLG), polyanhydrides, poly(N-vinyl pyrrolidone), poly(vinyl alcohol), polyacrylamide, poly(ethylene glycol), polyactides (PLA), poly(lactide-co-glycolides)(PLGA), and polyorthoesters. In a preferred embodiment, the polymer used in a sustained release formulation is inert, free of leachable impurities, stable on storage, sterile, and biodegradable. In yet another embodiment, a controlled or sustained release system can be placed in proximity to the therapeutic target, thus requiring only a fraction of the systematic dose (see, e.g., Goodson, in Medical Applications of Controlled Release, supra, vol. 2, pp. 115-138 (1984)).

Carriers for use with such pharmaceutical compositions are biocompatible, and may also be biodegradable. In certain embodiments, the formulation preferably provides a relatively constant level of active component release. In other embodiments, however, a more rapid rate of release immediately upon administration may be desired. The formulation of such compositions is well within the level of ordinary skill in the art using known techniques. Illustrative carriers useful in this regard include microparticles of poly(lactide-co-glycolide), polyacrylate, latex, starch, cellulose, dextran and the like. Other illustrative delayed-release carriers include supramolecular biovectors, which comprise a non-liquid hydrophilic core (e.g., a cross-linked polysaccharide or oligosaccharide) and, optionally, an external layer comprising an amphiphilic compound, such as a phospholipid (see e.g., U.S. Pat. No. 5,151,254 and PCT applications WO 94/20078, WO/94/23701 and WO 96/06638). The amount of active compound contained within a sustained release formulation depends upon the site of implantation, the rate and expected duration of release and the nature of the condition to be treated or prevented.

The compounds of the subject invention are administered to an individual in an effective amount or a pharmaceutically effective amount, to effect or enhance the individual's immune response. As used herein, "effective amount" or "pharmaceutically effective amount" is that amount which shows a response over and above the vehicle or negative controls. An "adjuvant-effective amount" is that amount of the compound in question that, when administered in conjunction with an antigen, shows a response over and above that produced by the antigen alone. The precise dosage of the compounds of the subject invention to be administered to a patient will depend upon the particular compound used, the route of administration, the pharmaceutical composition, and the patient. For example, when administered subcutaneously to enhance an antibody response, the amount of compound used is from 1 to about 250 micrograms, preferably from about 25 to about 50 micrograms based upon administration to a typical 70 kg adult patient.

In another embodiment, illustrative immunogenic compositions, e.g., immunogenic and/or vaccine compositions, of the present invention comprise DNA encoding one or more of the polypeptides as described above, such that the polypeptide is generated in situ. As noted above, the polynucleotide may be administered within any of a variety of delivery systems known to those of ordinary skill in the art. Indeed, numerous gene delivery techniques are well known in the art, such as those described by Rolland, Crit. Rev. Therap. Drug Carrier Systems 15:143-198, 1998, and references cited therein. Appropriate polynucleotide expression systems will, of course, contain the necessary regulatory DNA regulatory sequences for expression in a patient (such as a suitable promoter and terminating signal).

Therefore, in certain embodiments, polynucleotides encoding immunogenic polypeptides described herein are introduced into suitable mammalian host cells for expression using any of a number of known viral-based systems. In one illustrative embodiment, retroviruses provide a convenient and effective platform for gene delivery systems. A selected nucleotide sequence encoding a polypeptide of the present invention can be inserted into a vector and packaged in retroviral particles using techniques known in the art. The recombinant virus can then be isolated and delivered to a subject. A number of illustrative retroviral systems have been described (e.g., U.S. Pat. No. 5,219,740; Miller and Rosman (1989) BioTechniques 7:980-990; Miller, A. D. (1990) Human Gene Therapy 1:5-14; Scarpa et al. (1991) Virology 180:849-852; Burns et al. (1993) Proc. Natl. Acad. Sci. USA 90:8033-8037; and Boris-Lawrie and Temin (1993) Cur. Opin. Genet. Develop. 3:102-109.

In addition, a number of illustrative adenovirus-based systems have also been described. Unlike retroviruses which integrate into the host genome, adenoviruses persist extrachromosomally thus minimizing the risks associated with insertional mutagenesis (Haj-Ahmad and Graham (1986) J. Virol. 57:267-274; Bett et al. (1993) J. Virol. 67:5911-5921; Mittereder et al. (1994) Human Gene Therapy 5:717-729; Seth et al. (1994) J. Virol. 68:933-940; Barr et al. (1994) Gene Therapy 1:51-58; Berkner, K. L. (1988) BioTechniques 6:616-629; and Rich et al. (1993) Human Gene Therapy 4:461-476).

Various adeno-associated virus (AAV) vector systems have also been developed for polynucleotide delivery. AAV vectors can be readily constructed using techniques well known in the art. See, e.g., U.S. Pat. Nos. 5,173,414 and 5,139,941; International Publication Nos. WO 92/01070 and WO 93/03769; Lebkowski et al. (1988) Molec. Cell. Biol. 8:3988-3996; Vincent et al. (1990) Vaccines 90 (Cold Spring Harbor Laboratory Press); Carter, B. J. (1992) Current Opinion in Biotechnology 3:533-539; Muzyczka, N. (1992) Current Topics in Microbiol. and Immunol. 158:97-129; Kotin, R. M. (1994) Human Gene Therapy 5:793-801; Shelling and Smith (1994) Gene Therapy 1:165-169; and Zhou et al. (1994) J. Exp. Med. 179:1867-1875.

Additional viral vectors useful for delivering the polynucleotides encoding polypeptides of the present invention by gene transfer include those derived from the pox family of viruses, such as vaccinia virus and avian poxvirus. By way of example, vaccinia virus recombinants expressing the novel molecules can be constructed as follows. The DNA encoding a polypeptide is first inserted into an appropriate vector so that it is adjacent to a vaccinia promoter and flanking vaccinia DNA sequences, such as the sequence encoding thymidine kinase (TK). This vector is then used to transfect cells that are simultaneously infected with vaccinia. Homologous recombination serves to insert the vaccinia promoter plus the gene encoding the polypeptide of interest into the viral genome. The resulting TK.sup.(−) recombinant can be selected by culturing the cells in the presence of 5-bromodeoxyuridine and picking viral plaques resistant thereto.

A vaccinia-based infection/transfection system can be conveniently used to provide for inducible, transient expression or coexpression of one or more polypeptides described herein in host cells of an organism. In this particular system, cells are first infected in vitro with a vaccinia virus recombinant that encodes the bacteriophage T7 RNA polymerase. This polymerase displays exquisite specificity in that it only transcribes templates bearing T7 promoters. Following infection, cells are transfected with the polynucleotide or polynucleotides of interest, driven by a T7 promoter. The polymerase expressed in the cytoplasm from the vaccinia virus recombinant transcribes the transfected DNA into RNA that is then translated into polypeptide by the host translational machinery. The method provides for high level, transient, cytoplasmic production of large quantities of RNA and its translation products. See, e.g., Elroy-Stein and Moss, Proc. Natl. Acad. Sci. USA (1990) 87:6743-6747; Fuerst et al. Proc. Natl. Acad. Sci. USA (1986) 83:8122-8126.

Alternatively, avipoxviruses, such as the fowlpox and canarypox viruses, can also be used to deliver the coding sequences of interest. Recombinant avipox viruses, expressing immunogens from mammalian pathogens, are known to confer protective immunity when administered to non-avian species. The use of an Avipox vector is particularly desirable in human and other mammalian species since members of the Avipox genus can only productively replicate in susceptible avian species and therefore are not infective in mammalian cells. Methods for producing recombinant Avipoxviruses are known in the art and employ genetic recombination, as described above with respect to the production of vaccinia viruses. See, e.g., WO 91/12882; WO 89/03429; and WO 92/03545.

Any of a number of alphavirus vectors can also be used for delivery of polynucleotide compositions of the present invention, such as those vectors described in U.S. Pat. Nos. 5,843,723; 6,015,686; 6,008,035 and 6,015,694. Certain vectors based on Venezuelan Equine Encephalitis (VEE) can also be used, illustrative examples of which can be found in U.S. Pat. Nos. 5,505,947 and 5,643,576.

Moreover, molecular conjugate vectors, such as the adenovirus chimeric vectors described in Michael et al. J. Biol. Chem. (1993) 268:6866-6869 and Wagner et al. Proc. Natl. Acad. Sci. USA (1992) 89:6099-6103, can also be used for gene delivery under the invention.

Additional illustrative information on these and other known viral-based delivery systems can be found, for example, in Fisher-Hoch et al., *Proc. Natl. Acad. Sci. USA* 86:317-321, 1989; Flexner et al., *Ann. N.Y. Acad. Sci.* 569: 86-103, 1989; Flexner et al., *Vaccine* 8:17-21, 1990; U.S. Pat. Nos. 4,603,112, 4,769,330, and 5,017,487; WO 89/01973; U.S. Pat. No. 4,777,127; GB 2,200,651; EP 0,345,242; WO 91/02805; Berkner, *Biotechniques* 6:616-627, 1988; Rosenfeld et al., *Science* 252:431-434, 1991; Kolls et al., *Proc. Natl. Acad. Sci. USA* 91:215-219, 1994; Kass-Eisler et al., *Proc. Natl. Acad. Sci. USA* 90:11498-11502, 1993; Guzman et al., *Circulation* 88:2838-2848, 1993; and Guzman et al., *Cir. Res.* 73:1202-1207, 1993.

In certain embodiments, a polynucleotide may be integrated into the genome of a target cell. This integration may be in the specific location and orientation via homologous recombination (gene replacement) or it may be integrated in a random, non-specific location (gene augmentation). In yet further embodiments, the polynucleotide may be stably maintained in the cell as a separate, episomal segment of DNA. Such polynucleotide segments or "episomes" encode sequences sufficient to permit maintenance and replication independent of or in synchronization with the host cell cycle. The manner in which the expression construct is delivered to a cell and where in the cell the polynucleotide remains is dependent on the type of expression construct employed.

In another embodiment of the invention, a polynucleotide is administered/delivered as "naked" DNA, for example as described in Ulmer et al., *Science* 259:1745-1749, 1993 and reviewed by Cohen, *Science* 259:1691-1692, 1993. The uptake of naked DNA may be increased by coating the DNA onto biodegradable beads, which are efficiently transported into the cells.

In still another embodiment, a composition of the present invention can be delivered via a particle bombardment approach, many of which have been described. In one illustrative example, gas-driven particle acceleration can be achieved with devices such as those manufactured by Powderject Pharmaceuticals PLC (Oxford, UK) and Powderject Vaccines Inc. (Madison, Wis.), some examples of which are described in U.S. Pat. Nos. 5,846,796; 6,010,478; 5,865,796; 5,584,807; and EP Patent No. 0500 799. This approach offers a needle-free delivery approach wherein a dry powder formulation of microscopic particles, such as polynucleotide or polypeptide particles, are accelerated to high speed within a helium gas jet generated by a hand held device, propelling the particles into a target tissue of interest.

In a related embodiment, other devices and methods that may be useful for gas-driven needle-less injection of compositions of the present invention include those provided by Bioject, Inc. (Portland, Oreg.), some examples of which are described in U.S. Pat. Nos. 4,790,824; 5,064,413; 5,312,335; 5,383,851; 5,399,163; 5,520,639 and 5,993,412.

Within certain embodiments of the invention, the pharmaceutical composition is preferably one that induces an immune response predominantly of the Th1 type. High levels of Th1-type cytokines (e.g., IFN-γ, TNFα, IL-2 and IL-12) tend to favor the induction of cell-mediated immune responses to an administered antigen. In contrast, high levels of Th2-type cytokines (e.g., IL-4, IL-5, IL-6 and IL-10) tend to favor the induction of humoral immune responses. Following application of an immunogenic composition as provided herein, a patient will support an immune response that includes Th1- and Th2-type responses. Within a preferred embodiment, in which a response is predominantly Th1-type, the level of Th1-type cytokines will increase to a greater extent than the level of Th2-type cytokines. The levels of these cytokines may be readily assessed using standard assays. Alternatively, or in addition, high levels of Th2-type cytokines (e.g., IL-4, IL-5, IL-6 and IL-10) may be desired for certain therapeutic applications. The levels of these cytokines may be readily assessed using standard assays. For a review of the families of cytokines, see Mosmann and Coffinan, *Ann. Rev. Immunol.* 7:145-173, 1989.

Illustrative compositions for use in induction of Th1-type cytokines include, for example, a combination of CpG-containing oligonucleotides (in which the CpG dinucleotide is unmethylated) as described, for example, in WO 96/02555, WO 99/33488 and U.S. Pat. Nos. 6,008,200 and 5,856,462. Immunostimulatory DNA sequences are also described, for example, by Sato et al., *Science* 273:352, 1996. Other suitable immunostimulants comprise saponins, such as QS21 (Aquila Biopharmaceuticals Inc., Framingham, Mass.), and related saponin deriviatives and mimetics thereof.

Any of a variety of additional immunostimulants may be included in the compositions of this invention. For example, cytokines, such as GM-CSF, interferons or interleukins to further modulate an immune response of interest. Additionally, Montanide ISA 720 (Seppic, France), SAF (Chiron, Calif., United States), ISCOMS (CSL), MF-59 (Chiron), the SBAS series of adjuvants (e.g., SBAS-2 or SBAS-4, available from SmithKline Beecham, Rixensart, Belgium), and Enhanzyn™ immunostimulant (Corixa, Hamilton, Mont.). Polyoxyethylene ether immunostimulants, are described in WO 99/52549A1 and may be used as well.

The pharmaceutical compositions of the invention will often further comprise one or more buffers (e.g., neutral buffered saline or phosphate buffered saline), carbohydrates (e.g., glucose, mannose, sucrose or dextrans), mannitol, proteins, polypeptides or amino acids such as glycine, antioxidants, bacteriostats, chelating agents such as EDTA or glutathione, adjuvants (e.g., aluminum hydroxide), solutes that render the formulation isotonic, hypotonic or weakly hypertonic with the blood of a recipient, suspending agents, thickening agents and/or preservatives. Alternatively, compositions of the present invention may be formulated as a lyophilizate.

The pharmaceutical compositions described herein may be presented in unit-dose or multi-dose containers, such as sealed ampoules or vials. Such containers are typically sealed in such a way to preserve the sterility and stability of the formulation until use. In general, formulations may be stored as suspensions, solutions or emulsions in oily or aqueous vehicles. Alternatively, a pharmaceutical composition may be stored in a freeze-dried condition requiring only the addition of a sterile liquid carrier immediately prior to use.

The development of suitable dosing and treatment regimens for using the particular compositions described herein in a variety of treatment regimens, including e.g., oral, parenteral, intravenous, intranasal, and intramuscular administration and formulation, is well known in the art, some of which are briefly discussed below for general purposes of illustration.

In certain applications, the pharmaceutical compositions disclosed herein may be delivered via oral administration to an animal. As such, these compositions may be formulated with an inert diluent or with an assimilable edible carrier, or they may be enclosed in hard- or soft-shell gelatin capsule, or they may be compressed into tablets, or they may be incorporated directly with the food of the diet.

The active compounds may even be incorporated with excipients and used in the form of ingestible tablets, buccal tables, troches, capsules, elixirs, suspensions, syrups, wafers, and the like (see, for example, Mathiowitz et al., Nature 1997 Mar. 27; 386(6623):410-4; Hwang et al., Crit Rev Ther Drug Carrier Sits 1998; 15(3):243-84; U.S. Pat. No. 5,641,515; U.S. Pat. No. 5,580,579 and U.S. Pat. No. 5,792,451). Tablets, troches, pills, capsules and the like may also contain any of a variety of additional components, for example, a binder, such as gum tragacanth, acacia, cornstarch, or gelatin; excipients, such as dicalcium phosphate; a disintegrating agent, such as corn starch, potato starch, alginic acid and the like; a lubricant, such as magnesium stearate; and a sweetening agent, such as sucrose, lactose or saccharin may be added or a flavoring agent, such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar, or both. Of course, any material used in preparing any dosage unit form should be pharmaceutically pure and substantially non-toxic in the amounts employed. In addition, the active compounds may be incorporated into sustained-release preparation and formulations.

Typically, these formulations will contain at least about 0.1% of the active compound or more, although the percentage of the active ingredient(s) may, of course, be varied and may conveniently be between about 1 or 2% and about 60% or 70% or more of the weight or volume of the total formulation. Naturally, the amount of active compound(s) in each therapeutically useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

For oral administration the compositions of the present invention may alternatively be incorporated with one or more excipients in the form of a mouthwash, dentifrice, buccal tablet, oral spray, or sublingual orally-administered formulation. Alternatively, the active ingredient may be incorporated into an oral solution such as one containing sodium borate, glycerin and potassium bicarbonate, or dispersed in a dentifrice, or added in a therapeutically-effective amount to a composition that may include water, binders, abrasives, flavoring agents, foaming agents, and humectants. Alternatively the compositions may be fashioned into a tablet or solution form that may be placed under the tongue or otherwise dissolved in the mouth.

In certain circumstances it will be desirable to deliver the pharmaceutical compositions disclosed herein parenterally, intravenously, intramuscularly, or even intraperitoneally. Such approaches are well known to the skilled artisan, some of which are further described, for example, in U.S. Pat. No. 5,543,158; U.S. Pat. No. 5,641,515 and U.S. Pat. No. 5,399,363. In certain embodiments, solutions of the active compounds as free base or pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations generally will contain a preservative to prevent the growth of microorganisms.

Illustrative pharmaceutical forms suitable for injectable use include sterile aqueous solutions or dispersions and sterile powders for the extemporaneous preparation of sterile injectable solutions or dispersions (for example, see U.S. Pat. No. 5,466,468). In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and/or by the use of surfactants. The prevention of the action of microorganisms can be facilitated by various antibacterial and antifuigal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

In one embodiment, for parenteral administration in an aqueous solution, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, a sterile aqueous medium that can be employed will be known to those of skill in the art in light of the present disclosure. For example, one dosage may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. Moreover, for human administration, preparations will of course preferably meet sterility, pyrogenicity, and the general safety and purity standards as required by FDA Office of Biologics standards.

In another embodiment of the invention, the compositions disclosed herein may be formulated in a neutral or salt form. Illustrative pharmaceutically-acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, solutions will be administered in a manner compatible with the dosage formulation and in such amount as is therapeutically effective.

In certain embodiments, the pharmaceutical compositions may be delivered by intranasal sprays, inhalation, and/or other aerosol delivery vehicles. Methods for delivering genes, nucleic acids, and peptide compositions directly to the lungs via nasal aerosol sprays has been described, e.g., in U.S. Pat. No. 5,756,353 and U.S. Pat. No. 5,804,212. Likewise, the delivery of drugs using intranasal microparticle resins (Takenaga et al., J Controlled Release 1998 Mar. 2; 52(1-2):81-7) and lysophosphatidyl-glycerol compounds (U.S. Pat. No. 5,725,871) are also well-known in the pharmaceutical arts. Likewise, illustrative transmucosal drug delivery in the form of a polytetrafluoroetheylene support matrix is described in U.S. Pat. No. 5,780,045.

In certain embodiments, liposomes, nanocapsules, microparticles, lipid particles, vesicles, and the like, are used for the introduction of the compositions of the present invention into suitable host cells/organisms. In particular, the compositions of the present invention may be formulated for delivery either encapsulated in a lipid particle, a liposome, a vesicle, a nanosphere, or a nanoparticle or the like. Alternatively, compositions of the present invention can be bound, either covalently or non-covalently, to the surface of such carrier vehicles.

The formation and use of liposome and liposome-like preparations as potential drug carriers is generally known to those of skill in the art (see for example, Lasic, Trends Biotechnol 1998 July; 16(7):307-21; Takakura, Nippon Rinsho 1998 March; 56(3):691-5; Chandran et al., Indian J Exp Biol. 1997 August; 35(8):801-9; Margalit, Crit Rev Ther Drug Carrier Syst. 1995; 12(2-3):233-61; U.S. Pat. No. 5,567,434; U.S. Pat. No. 5,552,157; U.S. Pat. No. 5,565,213; U.S. Pat. No. 5,738,868 and U.S. Pat. No. 5,795,587).

Liposomes have been used successfully with a number of cell types that are normally difficult to transfect by other procedures, including T cell suspensions, primary hepatocyte cultures and PC 12 cells (Renneisen et al., J Biol. Chem. 1990 Sep. 25; 265(27):16337-42; Muller et al., DNA Cell Biol. 1990 April; 9(3):221-9). In addition, liposomes are free of the DNA length constraints that are typical of viral-based delivery systems. Liposomes have been used effectively to introduce genes, various drugs, radiotherapeutic agents, enzymes, viruses, transcription factors, allosteric effectors and the like, into a variety of cultured cell lines and animals. Furthermore, the use of liposomes does not appear to be associated with autoimmune responses or unacceptable toxicity after systemic delivery.

In certain embodiments, liposomes are formed from phospholipids that are dispersed in an aqueous medium and spontaneously form multilamellar concentric bilayer vesicles (also termed multilamellar vesicles (MLVs).

Alternatively, in other embodiments, the invention provides for pharmaceutically-acceptable nanocapsule formulations of the compositions of the present invention. Nanocapsules can generally entrap compounds in a stable and reproducible way (see, for example, Quintanar-Guerrero et al., Drug Dev Ind Pharm. 1998 December; 24(12):1113-28). To avoid side effects due to intracellular polymeric overloading, such ultrafine particles (sized around 0.1 µm) may be designed using polymers able to be degraded in vivo. Such particles can be made as described, for example, by Couvreur et al., Crit Rev Ther Drug Carrier Syst. 1988; 5(1):1-20; zur Muhlen et al., Eur J Pharm Biopharm. 1998 March; 45(2): 149-55; Zambaux et al. J Controlled Release. 1998 Jan. 2; 50(1-3):31-40; and U.S. Pat. No. 5,145,684.

Cancer Therapies

Immunologic approaches to cancer therapy are based on the recognition that cancer cells can often evade the body's defenses against aberrant or foreign cells and molecules, and that these defenses might be therapeutically stimulated to regain the lost ground, e.g. pgs. 623-648 in Klein, Immunology (Wiley-Interscience, New York, 1982). Numerous recent observations that various immune effectors can directly or indirectly inhibit growth of tumors has led to renewed interest in this approach to cancer therapy, e.g. Jager, et al., Oncology 2001; 60(1):1-7; Renner, et al., Ann Hematol 2000 December; 79(12):651-9.

Four-basic cell types whose function has been associated with antitumor cell immunity and the elimination of tumor cells from the body are: i) B-lymphocytes which secrete immunoglobulins into the blood plasma for identifying and labeling the nonself invader cells; ii) monocytes which secrete the complement proteins that are responsible for lysing and processing the immunoglobulin-coated target invader cells; iii) natural killer lymphocytes having two mechanisms for the destruction of tumor cells, antibody-dependent cellular cytotoxicity and natural killing; and iv) T-lymphocytes possessing antigen-specific receptors and having the capacity to recognize a tumor cell carrying complementary marker molecules (Schreiber, H., 1989, in Fundamental Immunology (ed). W. E. Paul, pp. 923-955).

Cancer immunotherapy generally focuses on inducing humoral immune responses, cellular immune responses, or both. Moreover, it is well established that induction of $CD4^+$ T helper cells is necessary in order to secondarily induce either antibodies or cytotoxic $CD8^+$ T cells. Polypeptide antigens that are selective or ideally specific for cancer cells offer a powerful approach for inducing immune responses against cancer, and are an important aspect of the present invention.

Therefore, in further aspects of the present invention, the pharmaceutical compositions described herein may be used to stimulate an immune response against cancer. Within such methods, the pharmaceutical compositions described herein are administered to a patient, typically a warm-blooded animal, preferably a human. A patient may or may not be afflicted with cancer. Pharmaceutical compositions and vaccines may be administered either prior to or following surgical removal of primary tumors and/or treatment such as administration of radiotherapy or conventional chemotherapeutic drugs. As discussed above, administration of the pharmaceutical compositions may be by any suitable method, including administration by intravenous, intraperitoneal, intramuscular, subcutaneous, intranasal, intradermal, anal, vaginal, topical and oral routes.

Within certain embodiments, immunotherapy may be active immunotherapy, in which treatment relies on the in vivo stimulation of the endogenous host immune system to react against tumors with the administration of immune response-modifying agents (such as polypeptides and polynucleotides as provided herein).

Routes and frequency of administration of the therapeutic compositions described herein, as well as dosage, will vary from individual to individual, and may be readily established using standard techniques. In general, the pharmaceutical compositions and vaccines may be administered by injection (e.g., intracutaneous, intramuscular, intravenous or subcutaneous), intranasally (e.g., by aspiration) or orally. Preferably, between 1 and 10 doses may be administered over a 52 week period. Preferably, 6 doses are administered, at intervals of 1 month, and booster vaccinations may be given periodically thereafter. Alternate protocols may be appropriate for individual patients. A suitable dose is an amount of a compound that, when administered as described above, is capable of promoting an anti-tumor immune response, and is at least 10-50% above the basal (i.e., untreated) level. Such response can be monitored by measuring the anti-tumor antibodies in a patient or by vaccine-dependent generation of cytolytic effector cells capable of killing the patient's tumor cells in vitro. Such vaccines should also be capable of causing an immune response that leads to an improved clinical outcome (e.g., more frequent remissions, complete or partial or longer disease-free survival) in vaccinated patients as compared to non-vaccinated patients. In general, for pharmaceutical compositions and vaccines comprising one or more polypeptides, the amount of each polypeptide present in a dose ranges from about 25 µg to 5 mg per kg of host. Suitable dose sizes will vary with the size of the patient, but will typically range from about 0.1 mL to about 5 mL.

In general, an appropriate dosage and treatment regimen provides the active compound(s) in an amount sufficient to provide therapeutic and/or prophylactic benefit. Such a response can be monitored by establishing an improved clinical outcome (e.g., more frequent remissions, complete or partial, or longer disease-free survival) in treated patients as compared to non-treated patients. Increases in preexisting immune responses to a tumor protein generally correlate with an improved clinical outcome. Such immune responses may generally be evaluated using standard proliferation, cytotoxicity or cytokine assays, which may be performed using samples obtained from a patient before and after treatment.

The present invention is further described by way of the following non-limiting Examples and Test Examples that are given for illustrative purposes only. All references cited herein are incorporated by reference in their entirety.

EXAMPLES

Example 1

Primary Fatty Acyl Chain Modifications

This example describes preparation of primary fatty acid derivatives having variable length primary fatty acyl chains, alone or in combination with variable secondary fatty acid chains. For example, compounds 1a-c and 2a-c, in which short ($C_6$) and medium ($C_{10}$) chain primary fatty acids are combined with short, medium, or long chain secondary fatty acids.

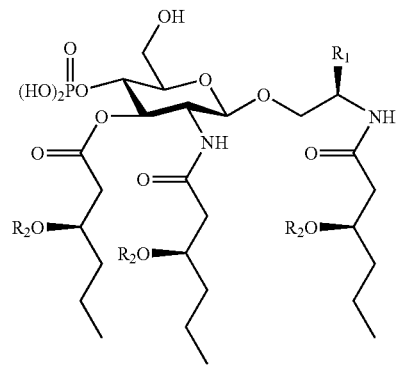

1a-c $R_1 = CO_2H$ or $CH_2OPO_3H_2$
$R_2 = C_6, C_{10}, C_{14}$ acyl

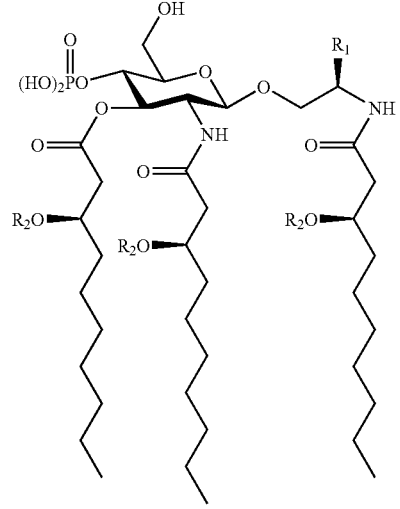

2a-c $R_1 = CO_2H$ or $CH_2OPO_3H_2$
$R_2 = C_6, C_{10}, C_{14}$ acyl

These compounds are prepared either using the well-established serine aglycon ($R_1=CO_2H$) or, alternatively, using a chemically more stable and ionizable serinol phosphate aglycon unit ($R_1=CH_2OPO_3H_2$). The seryl/serinol phosphate selection will be based on comparison of the biological activities of known seryl derivatives 3a,b with novel serinol phosphates 4a,b.

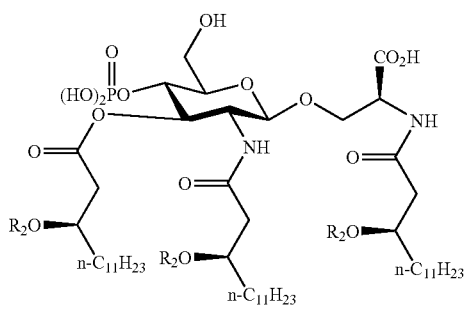

3a $R_2 = C_6$ acyl (RC-526)
3b $R_2 = C_{10}$ acyl (RC-527)

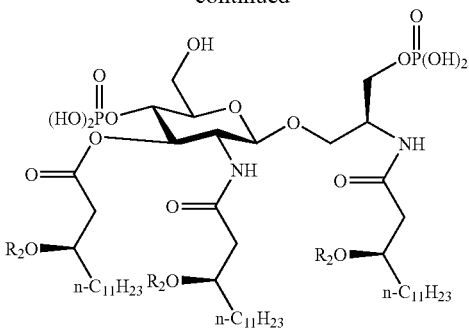

4a $R_2 = C_6$ acyl
4b $R_2 = C_{10}$ acyl

The primary chain-modified compounds derivatives are synthesized by a modification of a previously described method (B1 in Johnson et al., U.S. Pat. No. 6,355,251) employing a common advanced intermediate that allows introduction of the amide- and ester-linked acyloxy acids near the end of the synthesis (Scheme 1). The initial step in the synthesis is glycosylation of acceptor 6 with the known tetraacetate 5 (prepared in 4 steps from glucosamine) to give β-glycoside 7 and conversion of 7 to common advanced intermediate (CAI) 8, which is optimized for $R_1=CO_2Bn$. Selective 4-O-acylation and N-deprotection/acylation results in hexaacyl derivative 9, which is converted in 3-4 steps to 1a-c or 2a-c via phosphorylation and deblocking.

Scheme I

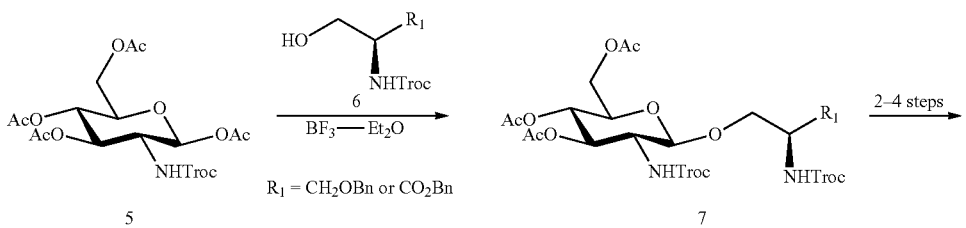

Troc = $CO_2CH_2CCl_3$
TBS = $Si(Me)_2Bu^t$

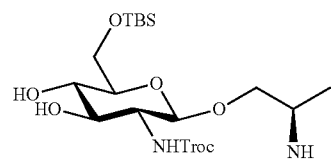

8
Common Advanced Intermediate 3 steps

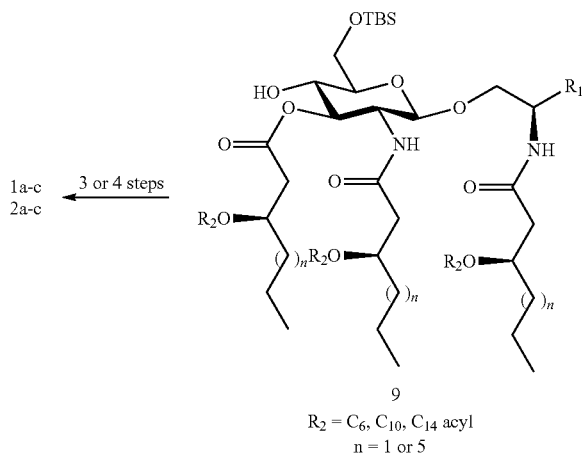

9
$R_2 = C_6, C_{10}, C_{14}$ acyl
n = 1 or 5

The requisite (R)-3-n-alkanoyloxyalkanoic acids are prepared according to Keegan et al., *Tetrahedron: Asymmetry;* 7(12):3559-3564, 1996, starting with the appropriate 3-oxo methyl esters. High chemical and diastereomeric purity of the products 1 and 2 is achieved by either normal phase chromatography on silica gel or, alternatively, via cellulose chromatography or liquid-liquid partition chromatography on Sephadex LH-20 gel. The purity of the isolated triethylammonium salts is established by spectroscopic (IR, $^1$H and $^{13}$C NMR) and physical (combustion analysis, FAB-MS) means, as well as by HPLC.

Example 2

Glycyl and phosphonooxyethyl (PE) Compounds

This example describes the synthesis of glycyl compounds 11a,b and phosphonooxyethyl (PE) compounds 12a,b, which are nearly regioisomeric with 3a,b and 4a,b.

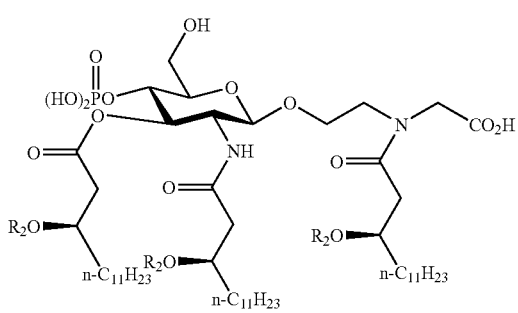

11a $R_2 = C_6$ acyl
11b $R_2 = C_{10}$ acyl

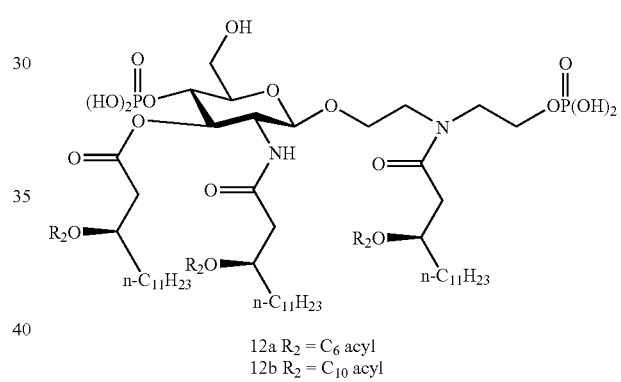

12a $R_2 = C_6$ acyl
12b $R_2 = C_{10}$ acyl

These compounds are most easily prepared by a more convergent synthesis than that outlined in Scheme I, in which a common $C_6$ or $C_{10}$ glycosyl donor 13 is coupled with an appropriate N-acylated (or, alternatively, N-Troc protected—not shown) acceptor unit 14 or 15 in the presence of silver ion to give β-glycosides 16 (Scheme II). The glycine acceptor 14 is prepared according to Bulusu et al., *J Med Chem;* 35(19): 3463-3469, 1992 from ethanolamine and benzyl (or t-butyl) bromoacetate followed by N-acylation or protection. The phosphate 15 is prepared by monophosphorylation of N-acylated (or protected) diethanolamine. N-deprotection/acylation or N,N-diacylation in case of Troc-protected aglycon (Jiang et al., *Tetrahedron;* 58(43):8833-8842, 2002) of the β-glycosides 16 and cleavage of the phenyl and other protecting groups of the resulting hexaacylated derivative 17 is expected to give the desired compounds 11a,b and 12a,b, which are isolated and characterized as their triethylammonium salts after chromatographic purification on silica or LH-20 gel or DEAE cellulose.

Compounds 16 are novel and form yet another aspect of this invention.

Scheme II

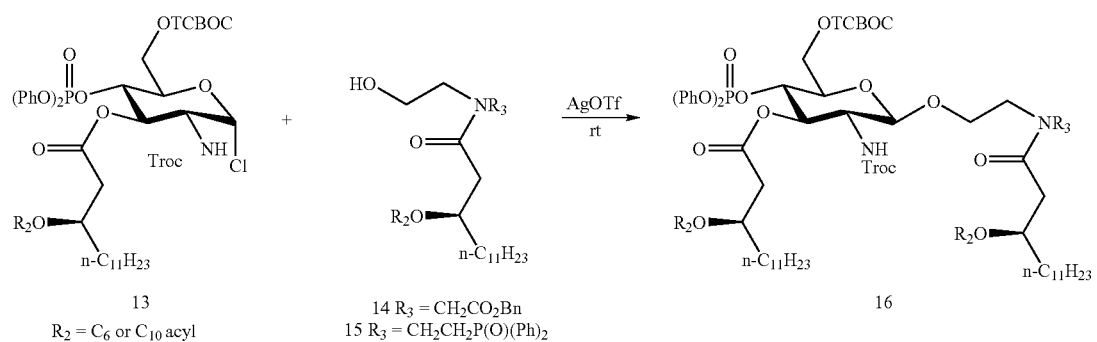

Example 3

Secondary Ether Lipids

This example describes synthesis of (R)-3-alkyloxytetradecanoic acid derivatives (18a,b) which are resistant to unfavorable metabolism and/or aqueous hydrolysis. To synthesize compounds 18a,b the ether lipid analogs of the secondary fatty acids present in compounds 3a,b or the corresponding serinol phosphates 4a,b must be prepared initially. As shown retrosynthetically in Scheme III, the synthesis of target molecules 18a,b can be achieved by substituting (R)-3-hexyloxytetradecanoic acid or (R)-3-decyloxytetradecanoic acid for the corresponding acyloxyacids beginning with selective 3-O-acylation of common advanced intermediate 8 in Scheme I and proceeding through intermediate 9 ($R_2$=$C_6$ or $C_{10}$ alkyl, n=9). The requisite alkyloxyacids 19 are synthesized from (R)-3-hydroxytetradecanoic acid or its phenacyl ester, intermediates in the acyloxyacid syntheses, by known methods in >50% overall yield (Keegan et al., *Tetrahedron: Asymmetry;* 7(12):3559-3564, 1996, Watanabe et al., *CarbohydrRes;* 332(3):257-277, 2001, Jiang., *Bioorg Med Chem Lett;* 12(16):2193-2196, 2002, Christ et al., U.S. Pat. No. 5,530,113. 1996).

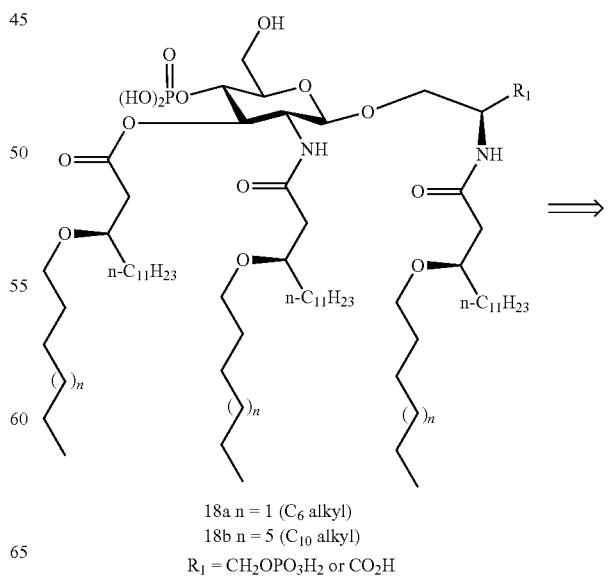

Scheme III

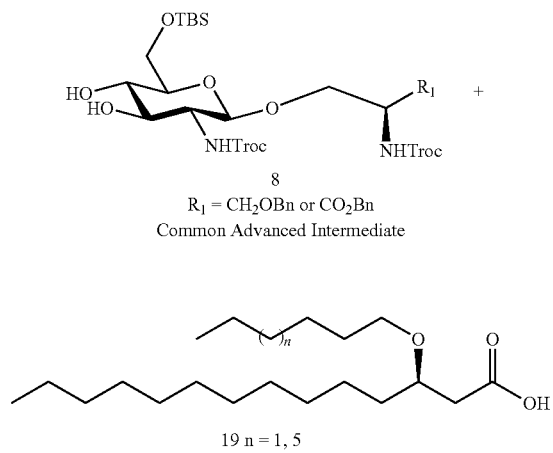

8
R₁ = CH₂OBn or CO₂Bn
Common Advanced Intermediate 19 n = 1, 5

Example 4

Primary and Secondary Ether Lipids

This example describes compounds (20a,b) containing a primary ether lipid at the C-3 sugar position as well as three secondary ether lipids. These compounds are synthesized by alkylation of acetonide 21, an intermediate in the synthesis of glycosyl donor 13 (Scheme II), with sulfonate 22, which in turn is generated in one step from the alcohol precursor of 19, to give diether 23 (Scheme IV). 4,6-Functionalization and anomeric activation provides glycosyl chloride 24, which is then processed as in Scheme II using the corresponding alkyloxyacids in the N-acylation steps. In an alternative scheme, the 2-azido[42] or 2-trifluoroacetamido[45] derivative can be employed in the 3-O-alkylation step.

Scheme IV

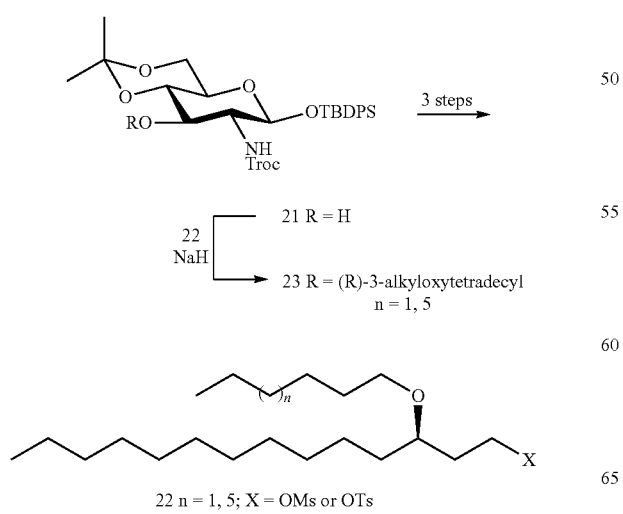

21 R = H
22 NaH
23 R = (R)-3-alkyloxytetradecyl
n = 1, 5

22 n = 1, 5; X = OMs or OTs

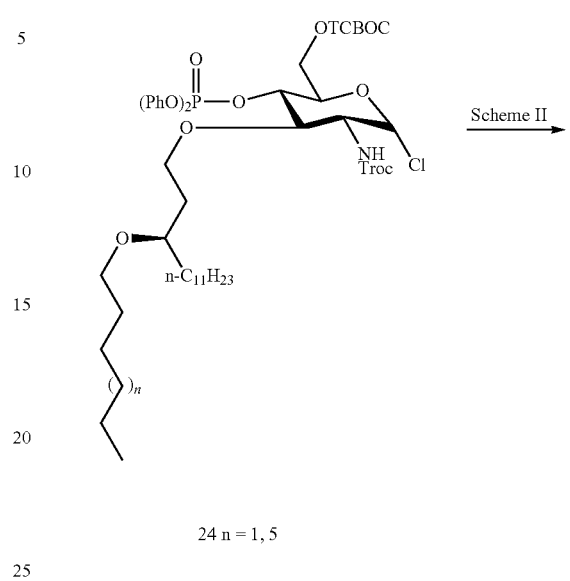

24 n = 1, 5

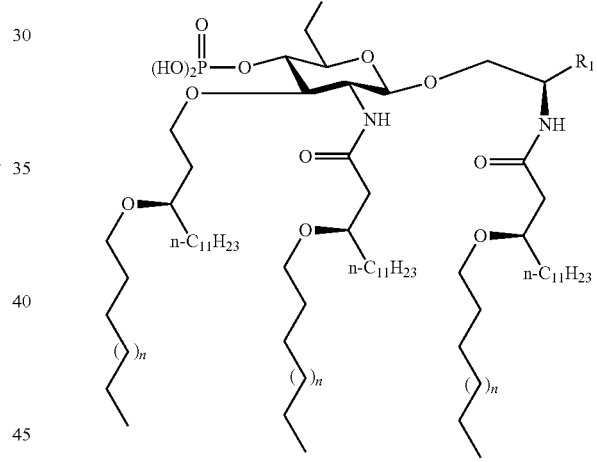

20a n = 1 (C₆ alkyl)
20b n = 5 (C₁₀ alkyl)

$R_1 = CH_2OPO_3H_2$ or $CO_2H$

Example 5

C-6 Modified Compounds

This example describes the compounds having a blocked 6-hydroxyl or a 6-substituent such as fluoro. In this example a methyl ether or a fluoro group is used in conjunction with seryl or serinol phosphate compounds 25a,b and 26a,b. As mentioned above, these compounds also form an aspect of the invention.

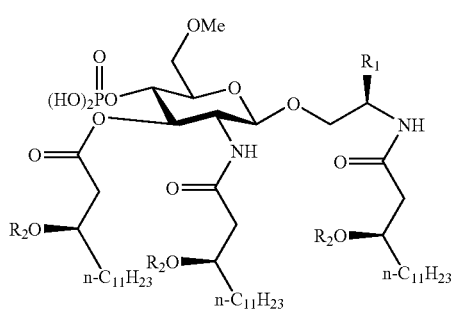

25a $R_2 = C_6$ acyl
25b $R_2 = C_{10}$ acyl
$R_1 = CO_2H$ or $CH_2OPO_3H_2$

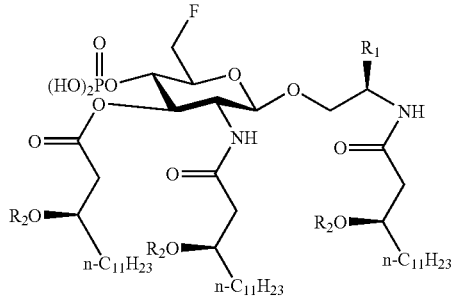

26a $R_2 = C_6$ acyl
26b $R_2 = C_{10}$ acyl

The compounds are prepared from diol 27 as shown in Scheme V. Intermediate 27, obtained in two steps from acetonide 21, is functionalized on the 6-position by known methods (Christ et al., U.S. Pat. No. 5,530,113, 1996; Watanabe et al., *CarbohydrRes;* 333(3):203-231, 2001) to give alcohol 28. Conversion of 28 to the chlorides 29 in two steps and elaboration according to Scheme II provides the target molecules 25a,b and 26a,b. Compounds with primary and/or secondary ether linkages as described in Example 4 above can be modified as described in this example to further protect the molecules against chemical and enzymatic degradation.

Scheme V

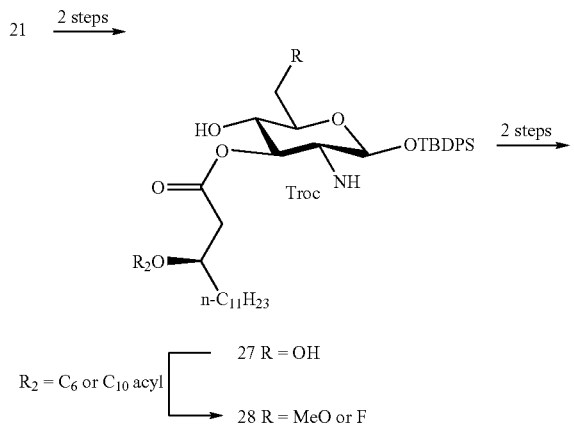

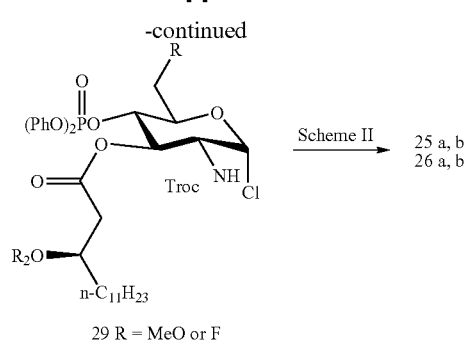

29 R = MeO or F

It is understood that the foregoing examples are merely illustrative of the present invention. Certain modifications of the compositions and/or methods employed may be made and still achieve the objectives of the invention. Such modifications are contemplated as within the scope of the claimed invention.

What is claimed is:

1. A compound having the formula:

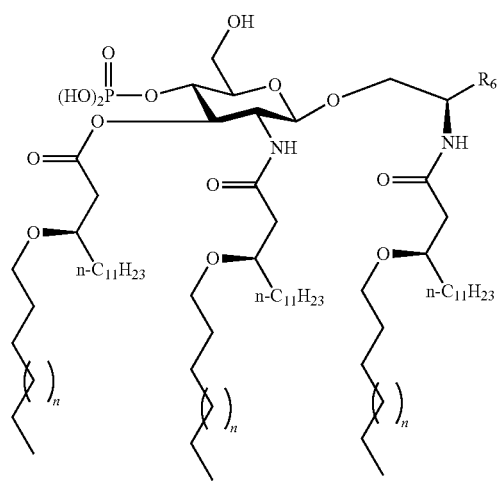

wherein n is 1 or 5 and $R_{13}$ is COOH or $CH_2OPO_3H_2$.

2. A compound according to claim 1 wherein n is 1.
3. A compound according to claim 1 wherein n is 5.
4. A compound according to claim 2, wherein $R_{13}$ is $CH_2OPO_3H_2$.
5. A compound according to claim 2, wherein $R_{13}$ is $CO_2H$.
6. A compound according to claim 3, wherein $R_{13}$ is $CH_2OPO_3H_2$.
7. A compound according to claim 3, wherein $R_{13}$ is $CO_2H$.
8. A pharmaceutical composition of matter comprising the compound according to claim 1, or a pharmaceutically acceptable salt thereof; and a pharmaceutically acceptable carrier.
9. A composition according to claim 8 suitable for mucosal administration.
10. A composition according to claim 8 suitable for intranasal administration.
11. A composition according to claim 8 further comprising an antigen, and comprising an adjuvant-effective amount of the compound of claim 1 or salt thereof.

* * * * *

UNITED STATES PATENT AND TRADEMARK OFFICE
CERTIFICATE OF CORRECTION

PATENT NO. : 7,960,522 B2  Page 1 of 1
APPLICATION NO. : 10/888683
DATED : June 14, 2011
INVENTOR(S) : David A. Johnson and David Persing It is certified that error appears in the above-identified patent and that said Letters Patent is hereby corrected as shown below:

In column 44, in the structure in Claim 1, "$R_6$" should read "$R_{13}$".

Signed and Sealed this
Third Day of May, 2016

Michelle K. Lee
*Director of the United States Patent and Trademark Office*